United States Patent
Arnold et al.

(10) Patent No.: US 12,185,928 B2
(45) Date of Patent: Jan. 7, 2025

(54) TROCAR INCISION CLOSURE KIT AND METHOD OF ASSEMBLING SAME

(71) Applicant: GORDIAN SURGICAL LTD, Misgav (IL)

(72) Inventors: Ofer Arnold, Maale' Zvia (IL); Hagay Weisbrod, Kibbutz Kinneret (IL); Roi Hamtsani, Alon HaGalil (IL)

(73) Assignee: GORDIAN SURGICAL LTD, Misgav (IL)

( * ) Notice: Subject to any disclaimer, the term of this patent is extended or adjusted under 35 U.S.C. 154(b) by 416 days.

(21) Appl. No.: 17/762,825

(22) PCT Filed: Sep. 24, 2020

(86) PCT No.: PCT/IL2020/051046
§ 371 (c)(1),
(2) Date: Mar. 23, 2022

(87) PCT Pub. No.: WO2021/059278
PCT Pub. Date: Apr. 1, 2021

(65) Prior Publication Data
US 2022/0395265 A1 Dec. 15, 2022

Related U.S. Application Data

(60) Provisional application No. 62/904,770, filed on Sep. 24, 2019.

(51) Int. Cl.
*A61B 17/00* (2006.01)
*A61B 17/04* (2006.01)
(52) U.S. Cl.
CPC ...... *A61B 17/0057* (2013.01); *A61B 17/0401* (2013.01); *A61B 2017/00637* (2013.01)

(58) Field of Classification Search
CPC ............ A61B 17/0057; A61B 17/0401; A61B 2017/00637; A61B 17/3417;
(Continued)

(56) References Cited

U.S. PATENT DOCUMENTS

| 8,109,943 B2 | 2/2012 | Boraiah et al. |
| 9,636,143 B2 | 5/2017 | Weisbrod et al. |

(Continued)

FOREIGN PATENT DOCUMENTS

EP    0568098 A2    11/1993

OTHER PUBLICATIONS

Jasson, Harrith M., "Laparoscopic cannula cone with means for cannula stabilization and wound closure", The Journal of the American Association of Gynecologic Laparoscopists, (May 31, 1998), vol. 5.2, pp. 183-185—English abstract.

*Primary Examiner* — Mohamed G Gabr
*Assistant Examiner* — Aman Kumar Mann
(74) *Attorney, Agent, or Firm* — William H. Dippert; Laurence A. Greenberg; Werner H. Stemer

(57) ABSTRACT

A kit for assembling an incision closing trocar comprising a cannula having a lumen, a proximal side, and a distal side is provided, the kit comprises an obturator comprising: a shaft having a distal end and a proximal end; at least two anchor recesses are provided near the distal end of the shaft, wherein each anchor recess retains a corresponding anchor; a handle provided at the proximal end of the obturator, is configured to actuate at least two pushers so as to push the corresponding anchors from the anchor recesses; and at least two holders, removably attached to the distal end of the obturator wherein each of the at least two holders holds a coiled or folded suture having a length and one end, wherein the one end of the suture is attached to the corresponding anchor, wherein the length of the suture can be pulled from (Continued)

the holders by removing and pulling away the holder from the obturator, wherein the obturator is sized to be inserted into the lumen of the cannula from the proximal side, together with the at least two holders so that the holders are exposed beyond the distal side when the obturator is fully inserted in the cannula, and then the holders can be removed from the obturator such that the sutures are outside the cannula.

7 Claims, 20 Drawing Sheets

(58) Field of Classification Search
CPC .... A61B 17/06123; A61B 2017/00663; A61B 2017/0409; A61B 2017/0416; A61B 2017/0417; A61B 2017/0464; A61B 2017/349; A61B 17/0469; A61B 17/3421; A61B 2017/0472; A61B 2017/3484; A61B 17/0482; A61B 17/3423
See application file for complete search history.

(56) References Cited

U.S. PATENT DOCUMENTS

| | | | |
|---|---|---|---|
| 9,955,997 | B2 | 5/2018 | Weisbrod et al. |
| 10,646,251 | B2 | 5/2020 | Weisbrod et al. |
| 2014/0066953 | A1 | 3/2014 | Keating et al. |
| 2015/0216514 | A1* | 8/2015 | Weisbrod ............ A61B 17/0057 606/232 |
| 2015/0223804 | A1* | 8/2015 | Wu ..................... A61B 17/0057 606/139 |
| 2017/0245846 | A1* | 8/2017 | Kim .................. A61B 17/06114 |
| 2018/0303470 | A1* | 10/2018 | Madsen ............. A61B 17/0469 |
| 2019/0000443 | A1 | 1/2019 | Jast et al. |
| 2020/0297339 | A1* | 9/2020 | Shaw ................. A61B 17/0401 |

* cited by examiner

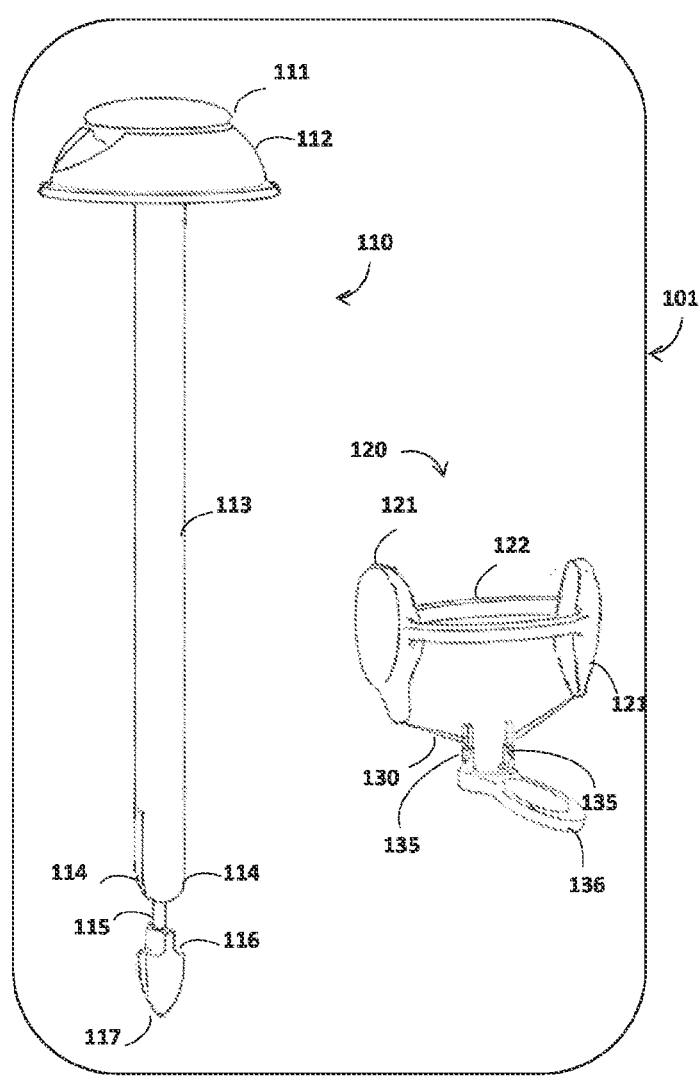
Fig. 1A(i)
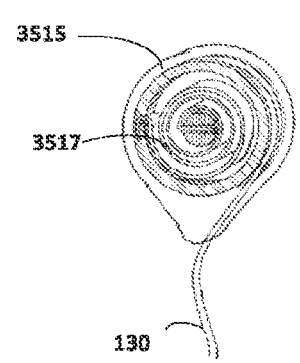
Fig. 1A(ii)

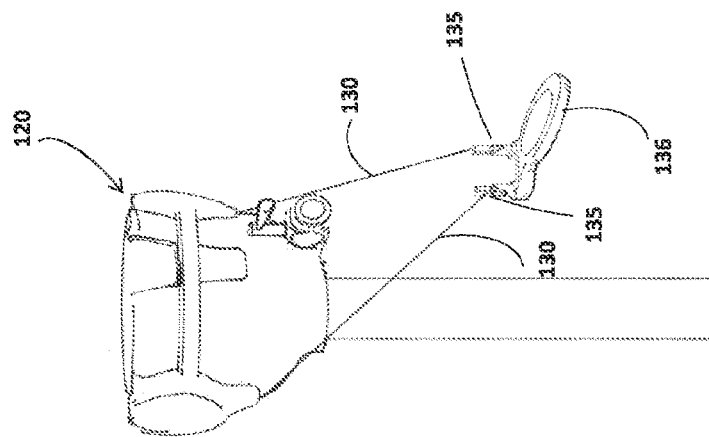
Fig. 1B(ii)
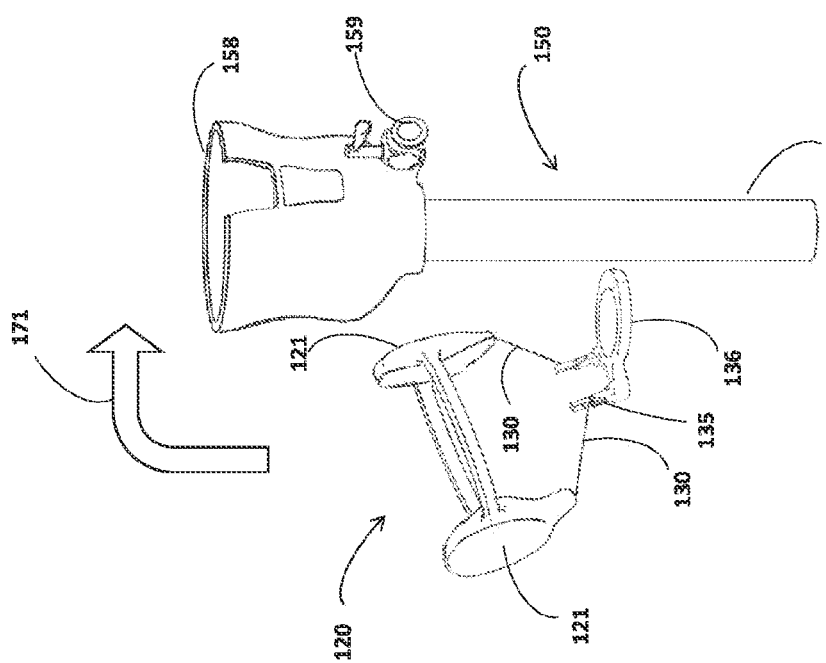
Fig. 1B(i)

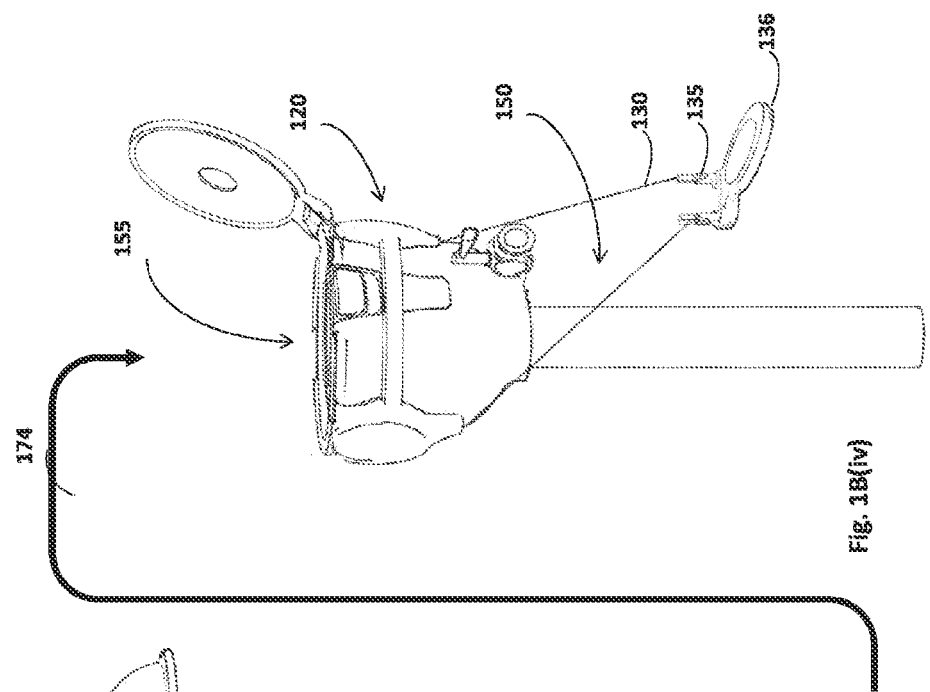
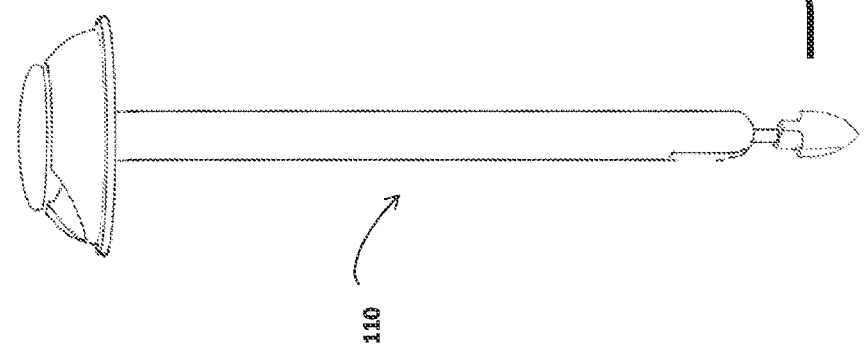
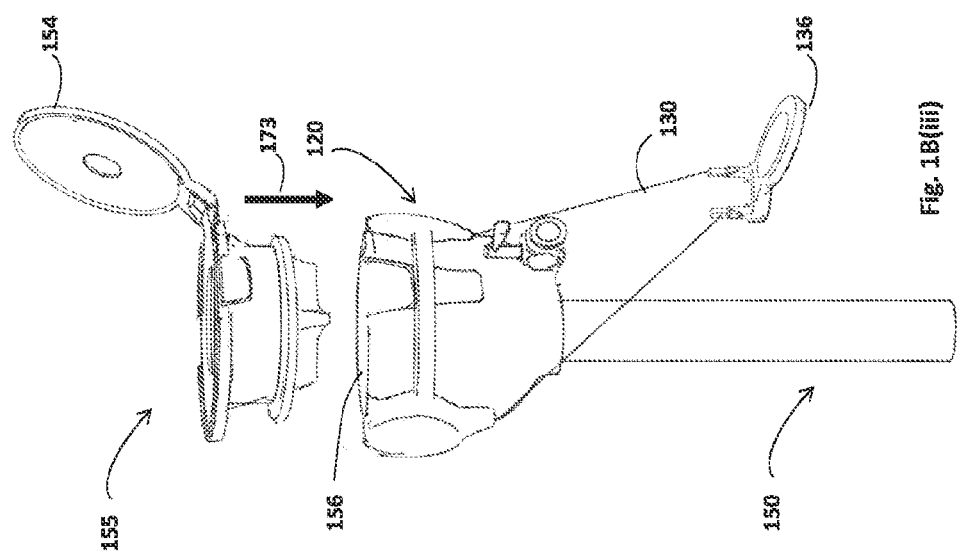
Fig. 1B(iv)
Fig. 1B(iii)

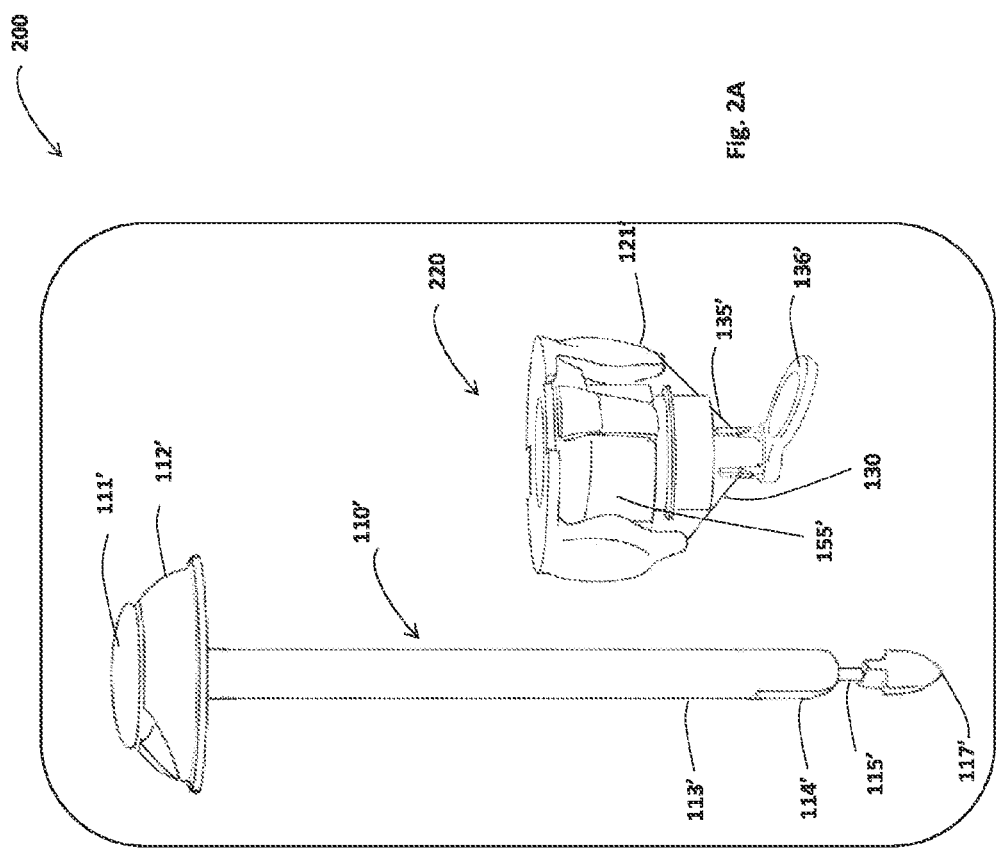

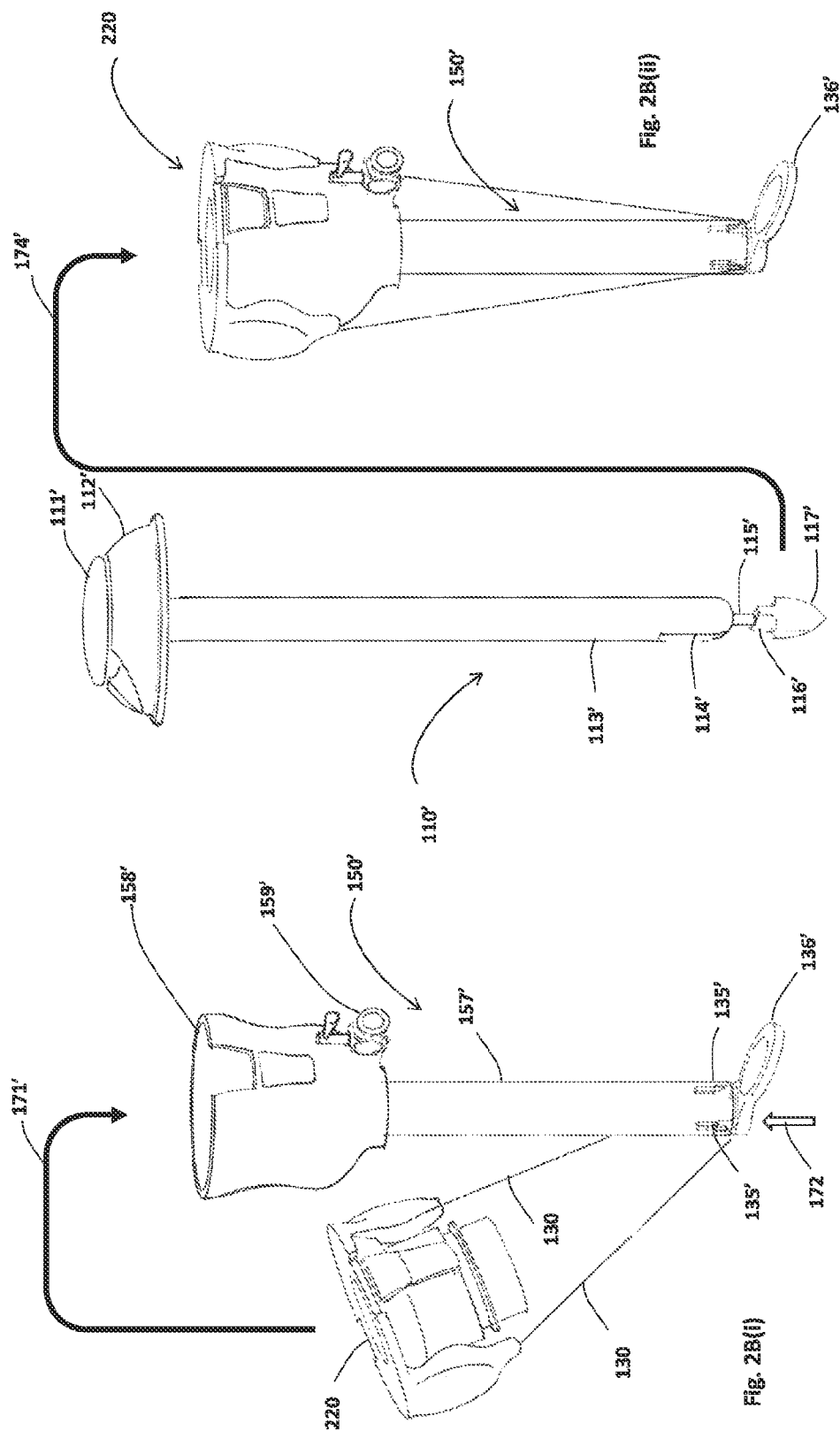

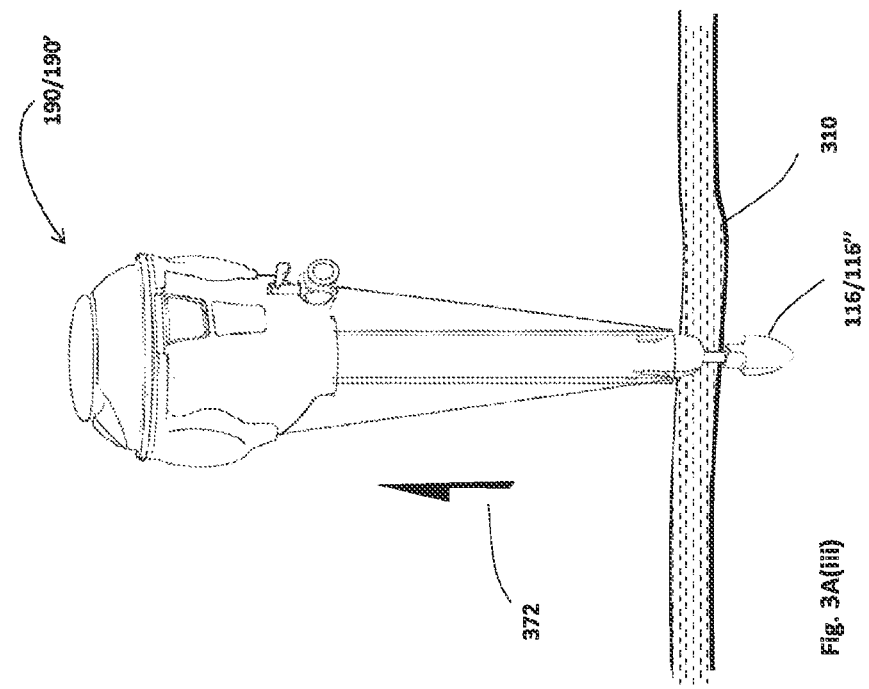
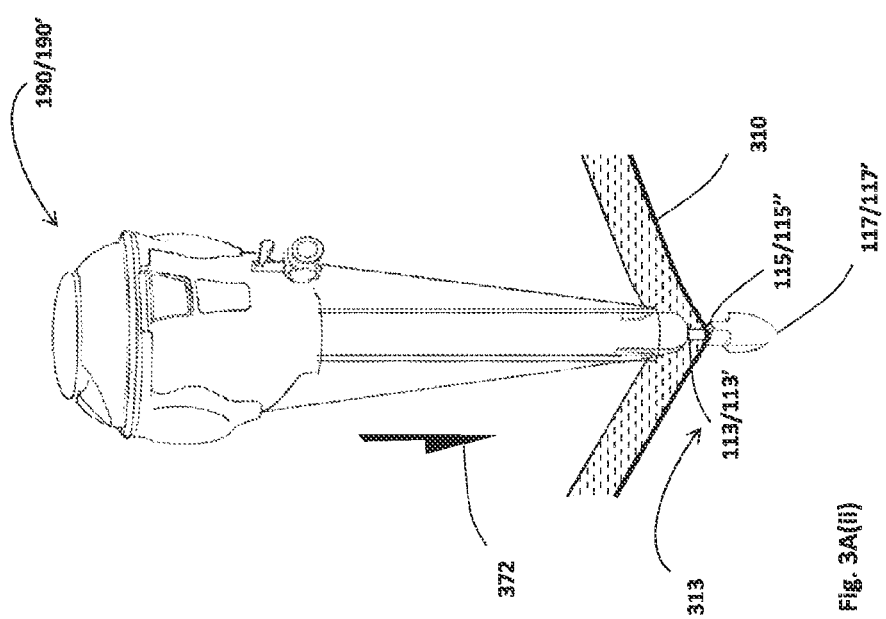

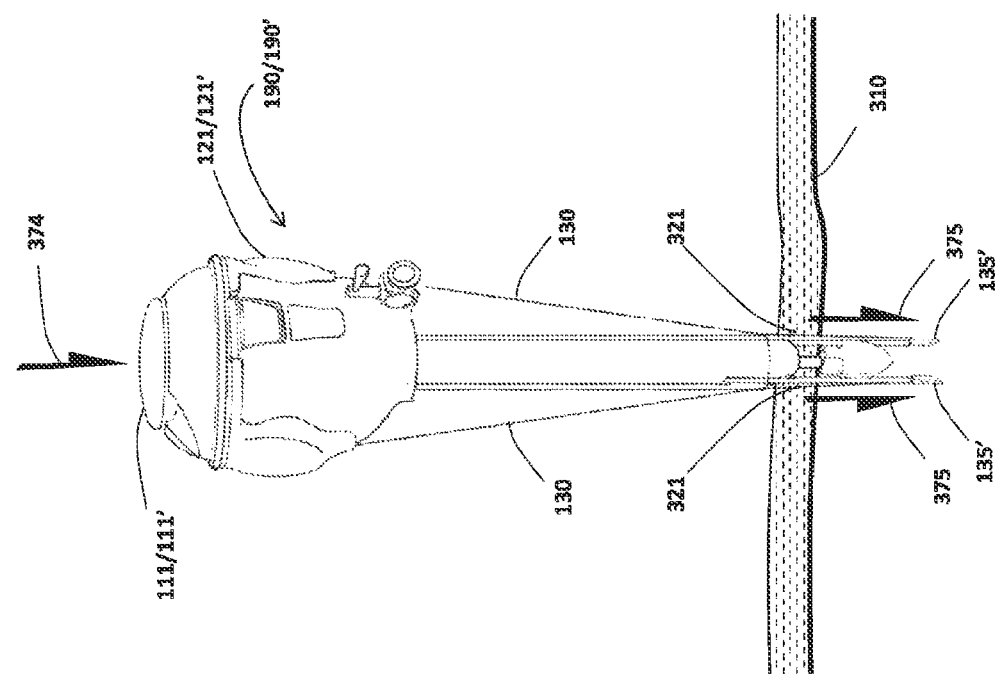
Fig. 3A(v)
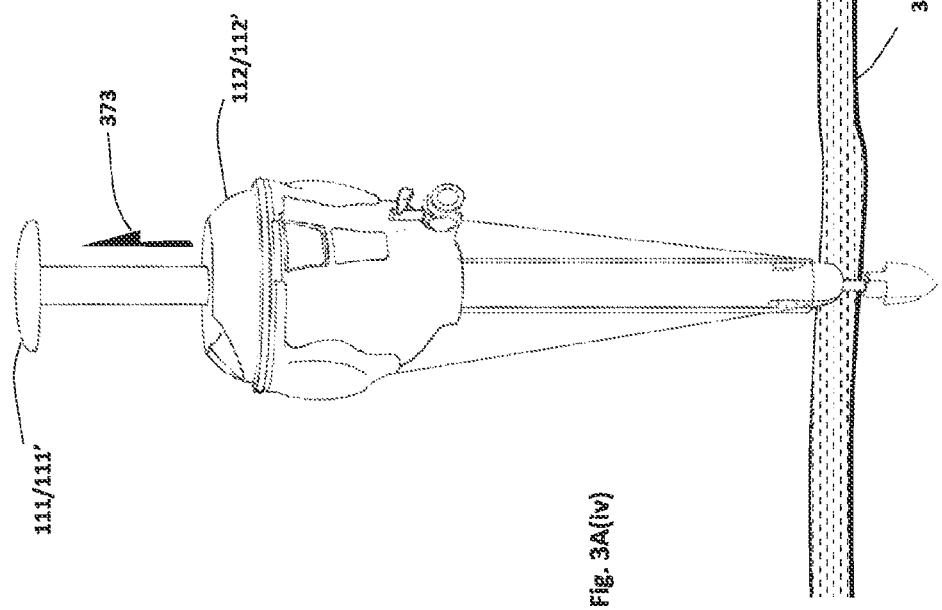
Fig. 3A(iv)

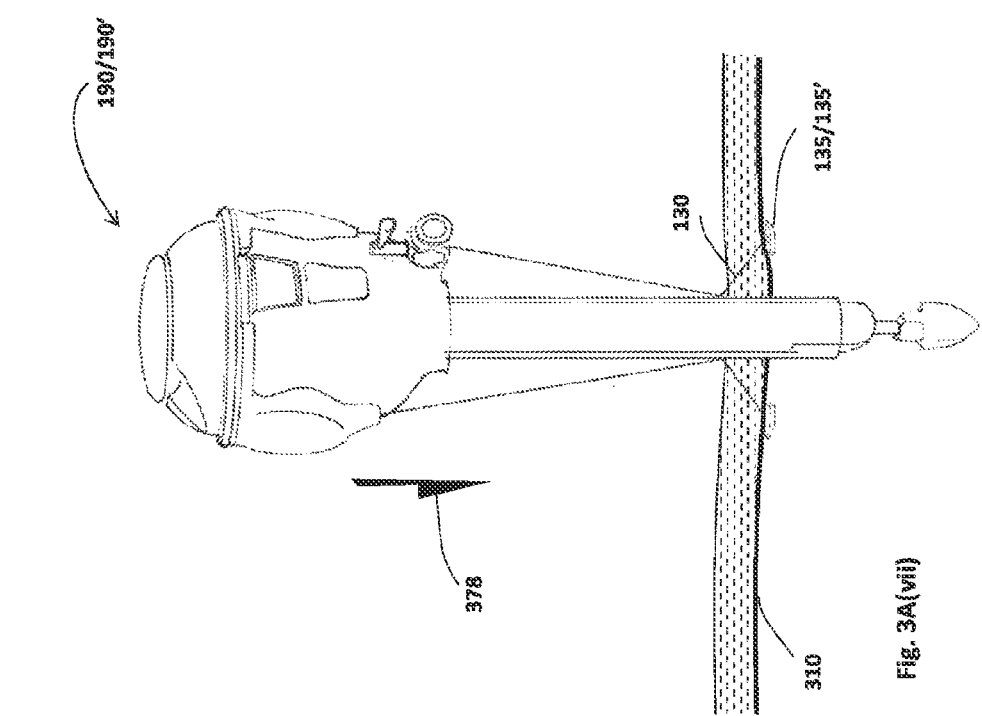
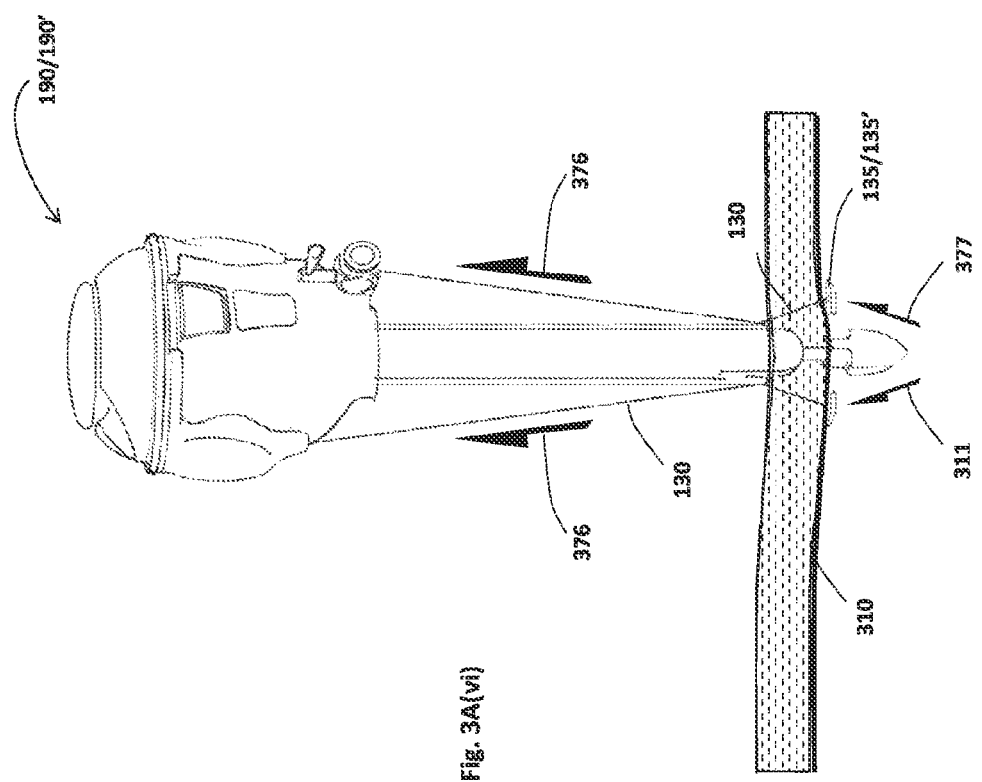

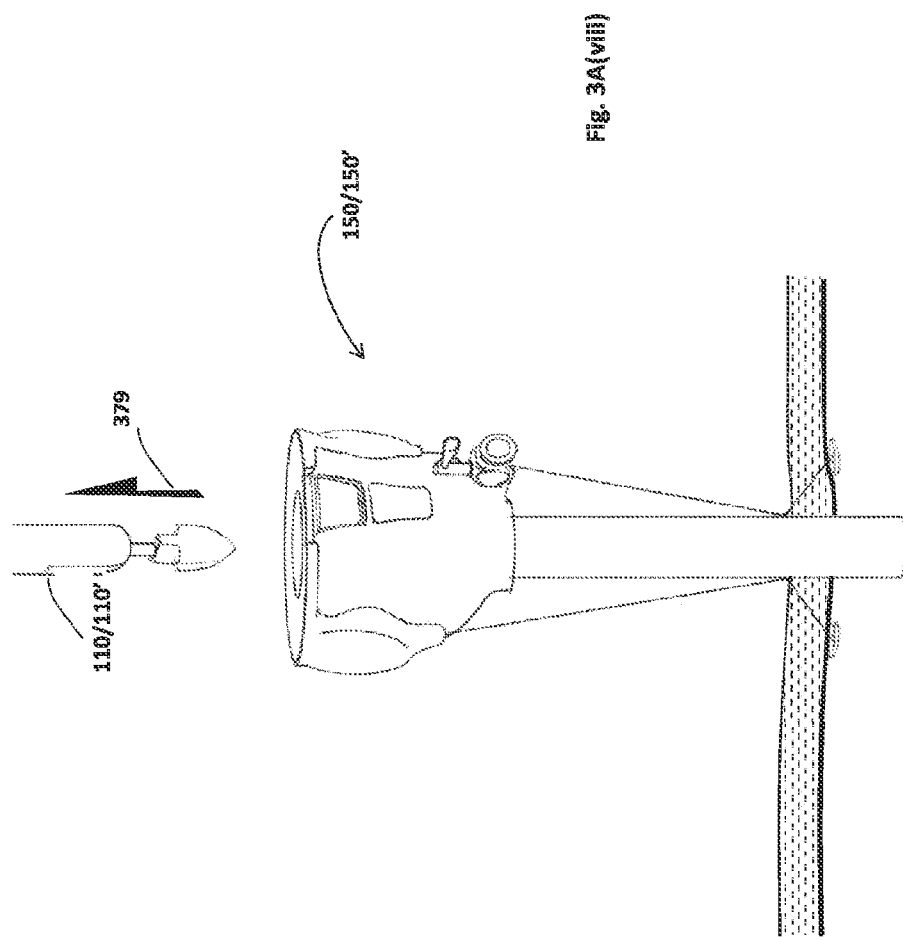

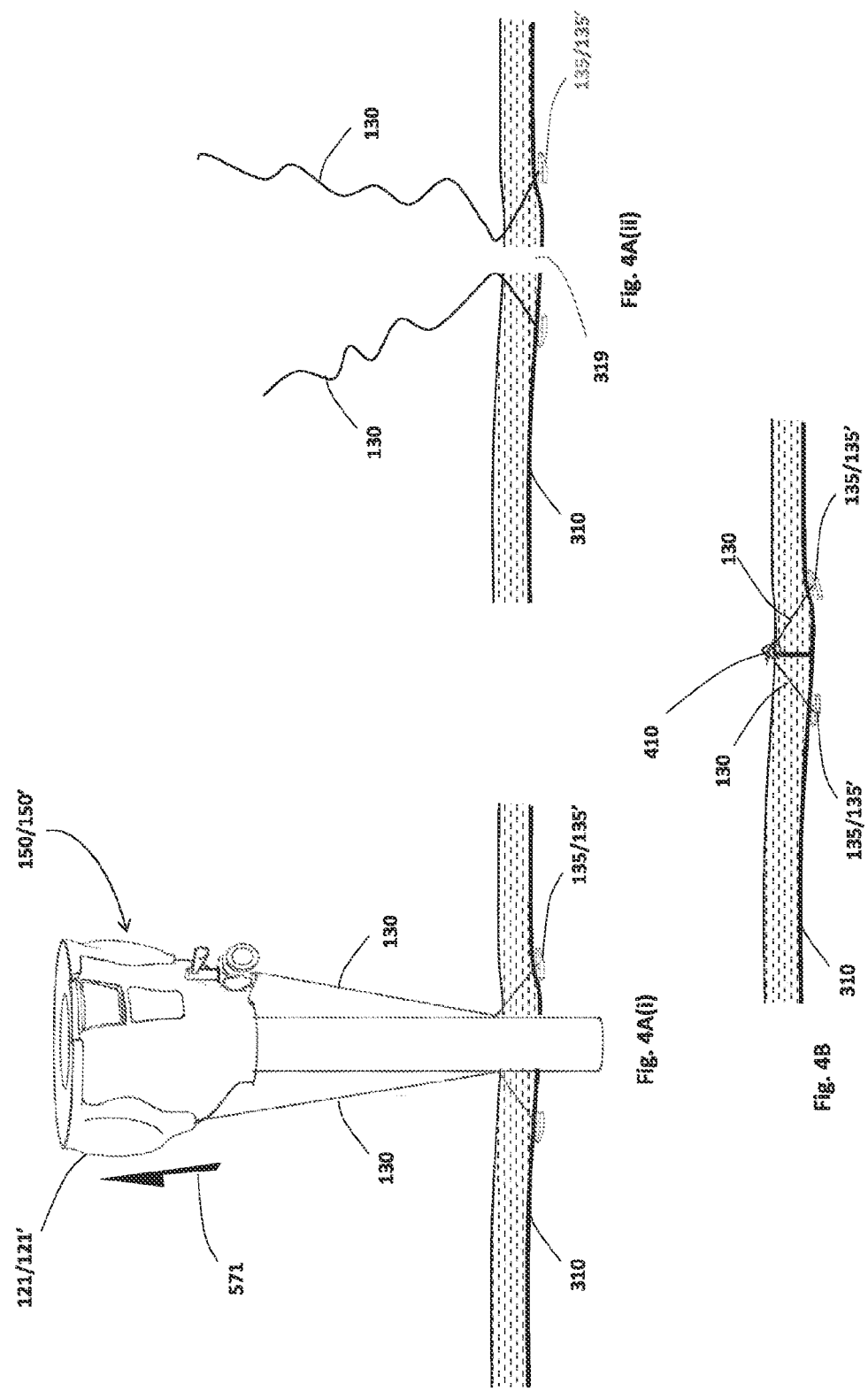

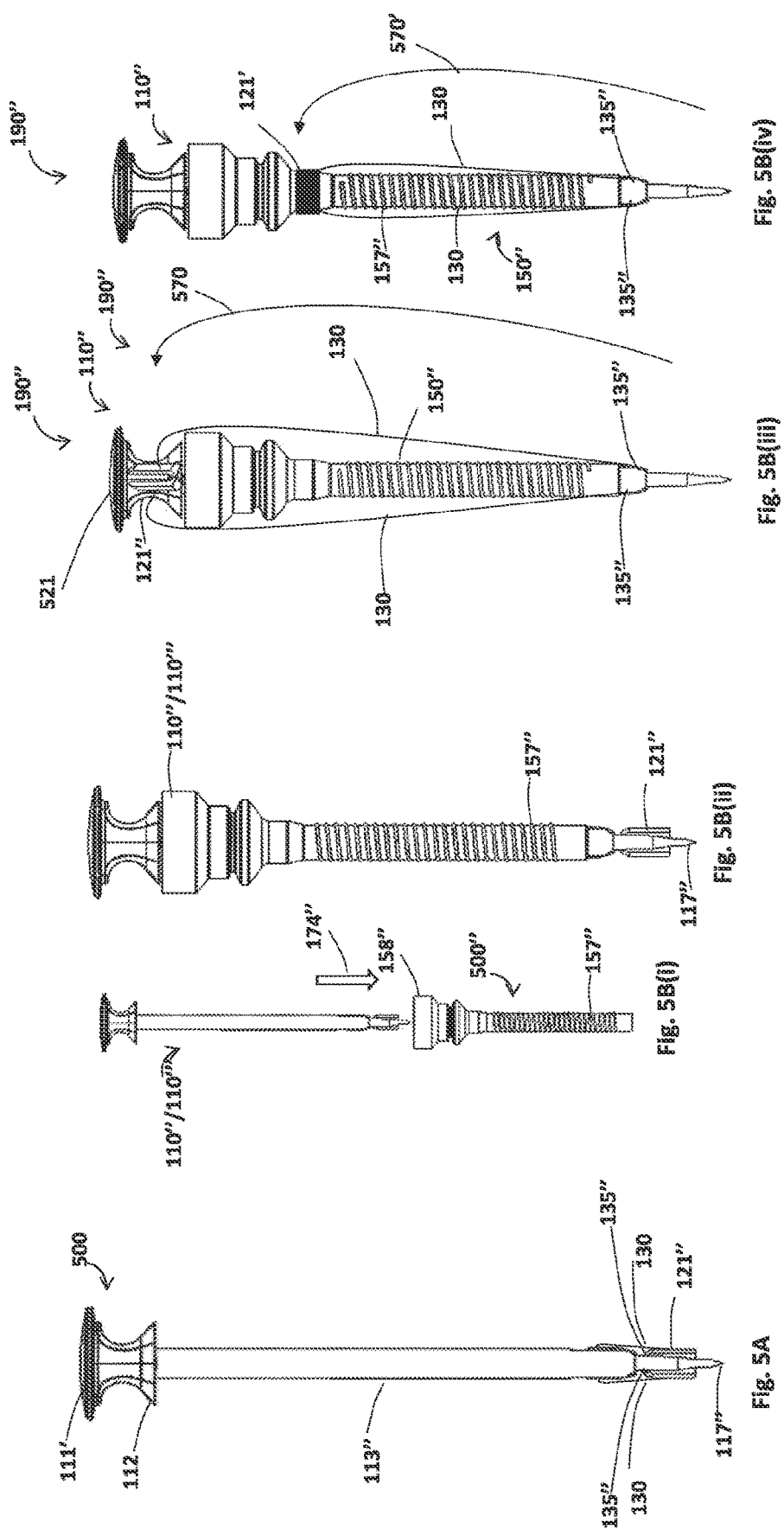

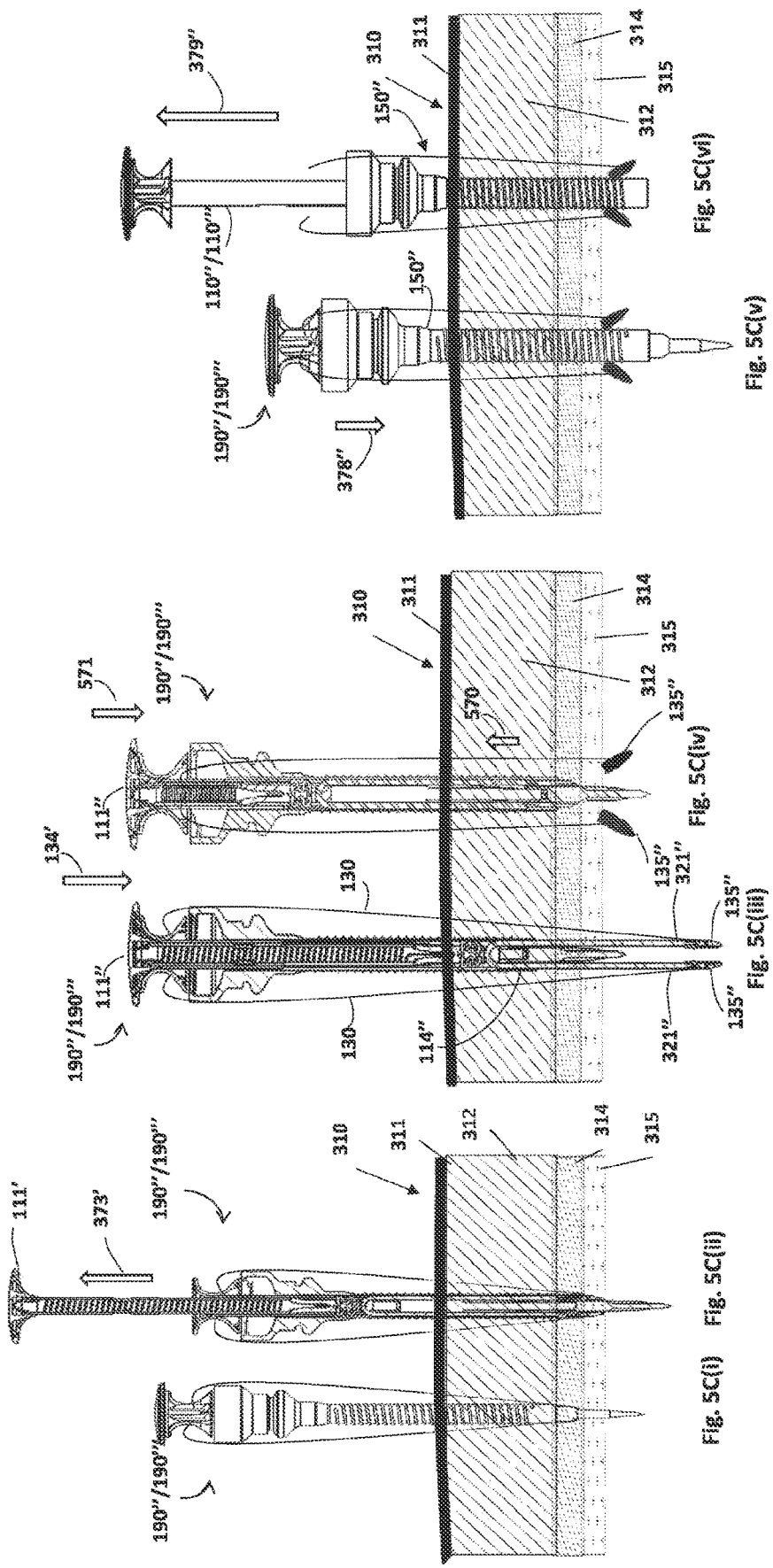

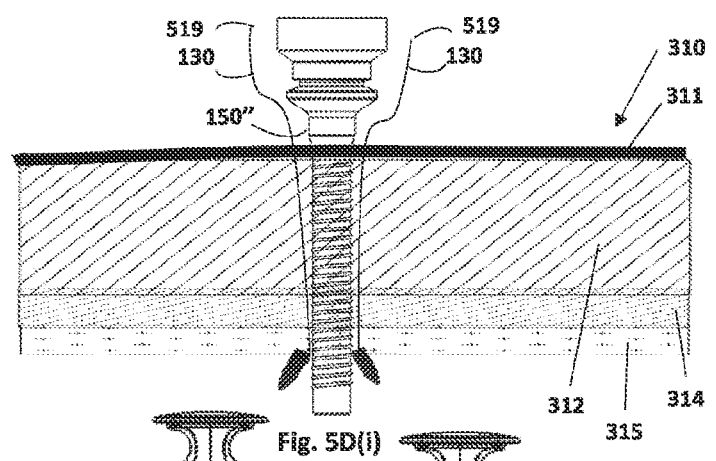
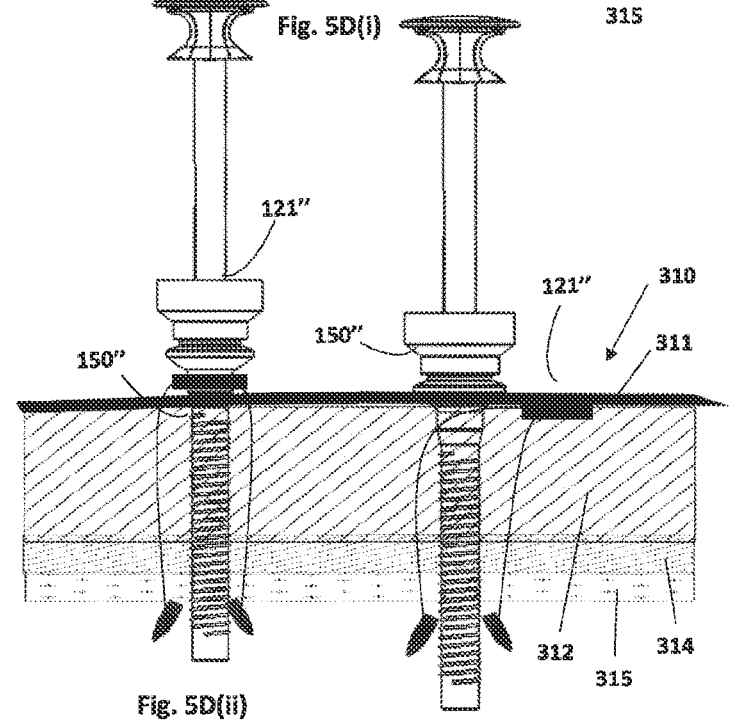
Fig. 5D(i)
Fig. 5D(ii)
Fig. 5D(iii)

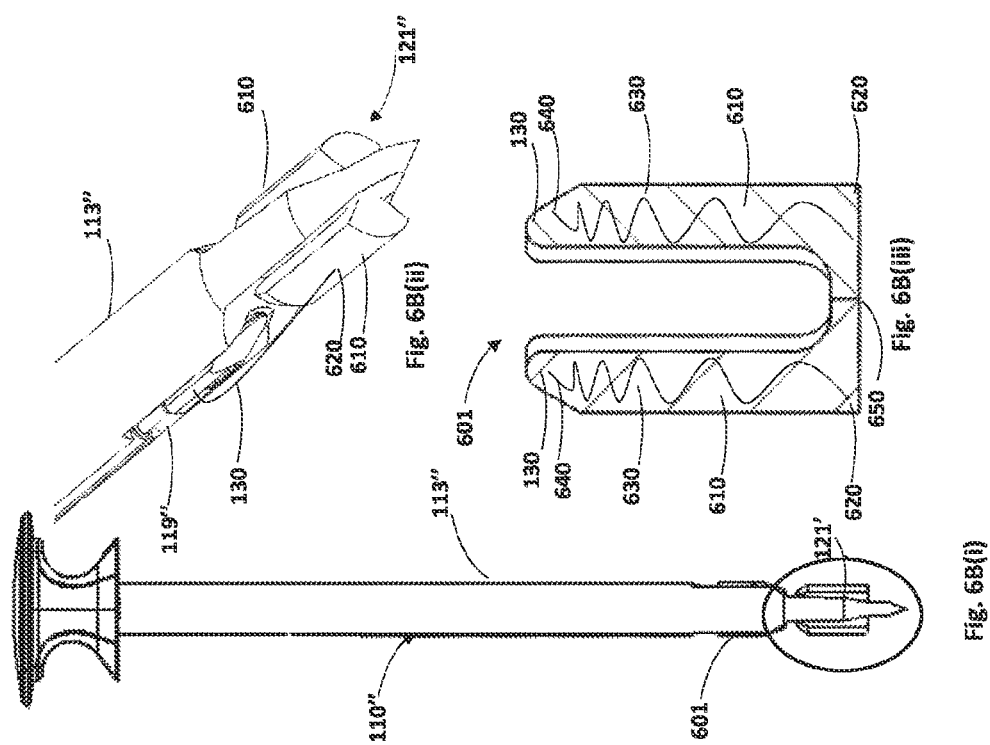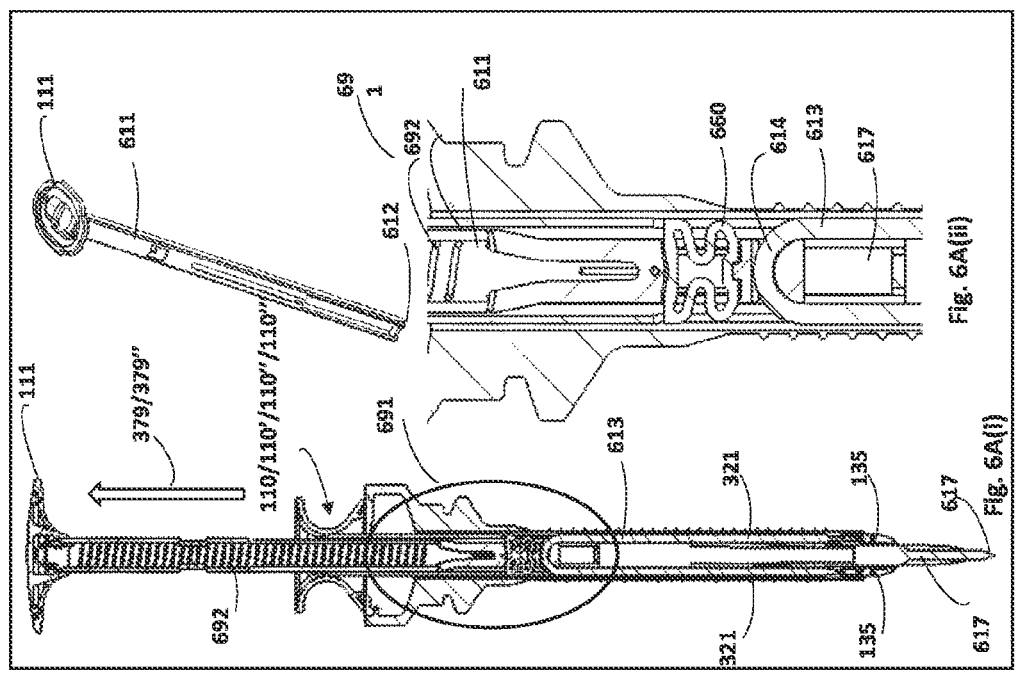

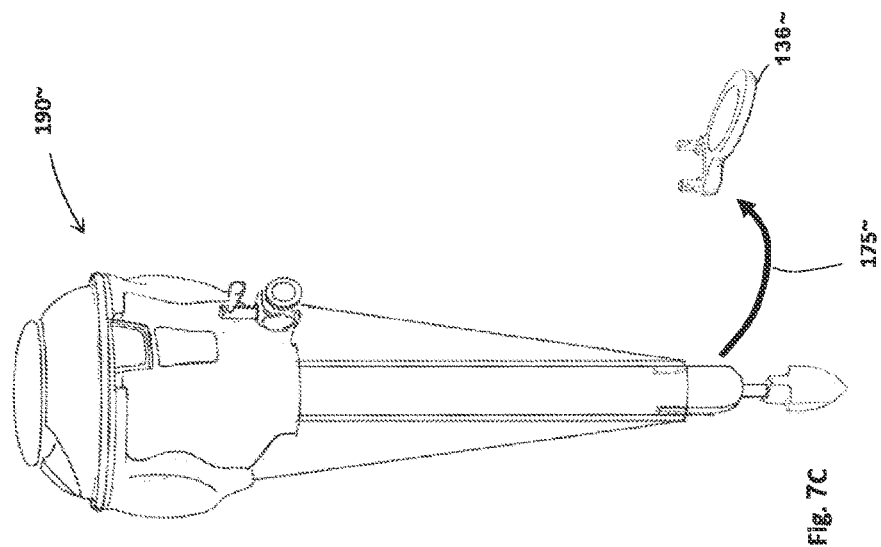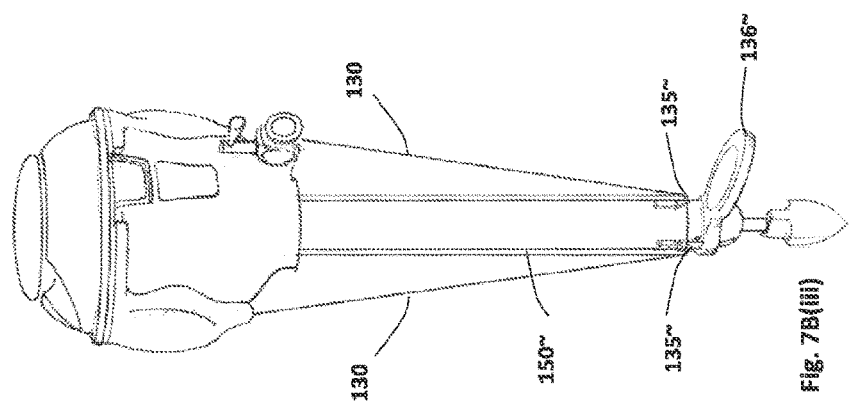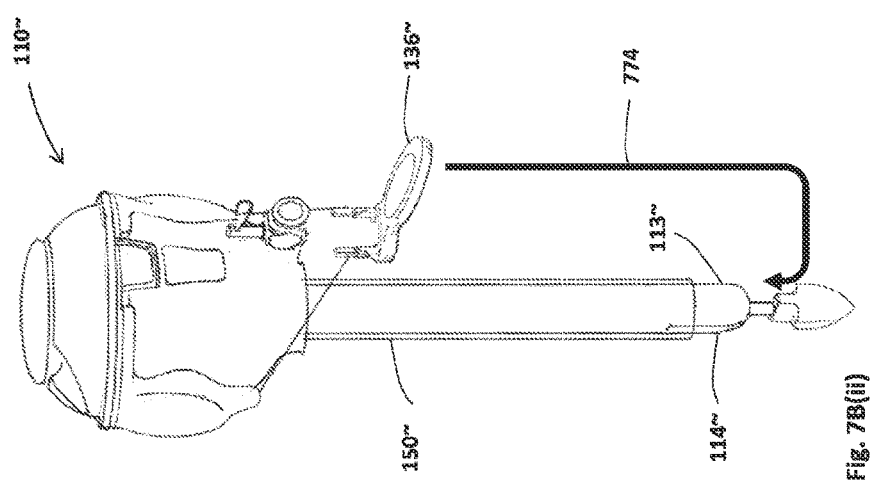

TROCAR INCISION CLOSURE KIT AND METHOD OF ASSEMBLING SAME

CROSS-REFERENCE TO RELATED PATENT APPLICATIONS

This patent application is a U.S. National Phase filing under 35 U.S.C. § 371 of PCT Patent Application No. PCT/IL2020/051046, filed Sep. 24, 2020, which is based upon and claims the priority of U.S. Provisional Patent Application Ser. No. 62/904,770, filed Sep. 24, 2019, each of which is incorporated herein by reference in its entirety.

TECHNICAL FIELD

The present invention relates to a trocar incised port closure and, more particularly, to an incision closure add-on kit to be used with a trocar and external cannula assembly for use in laparoscopic procedures.

BACKGROUND

Laparoscopic surgery commonly includes the use of a trocar for introducing a laparoscope or other surgical instruments through an incised port in the abdominal wall. Following the procedure, various techniques may be used to provide incision closure, with or without visual control. Sufficient closure of the port is of major significance for prevention of complications such as hernia.

The following publications disclose a trocar incision closure device:

U.S. Pat. Nos. 9,636,143, 9,955,997 and 10,646,251 to Weisbrod Hagay, et al. disclose a trocar adapted for insertion through a fascia layer of an abdominal wall, comprising a proximal end configured for handling by a user; a distal end configured for insertion into tissue; and a shaft extending in between the proximal end and distal end, wherein the shaft comprises a narrow portion proximal to the distal end, the narrow portion defining at least one recess shaped and sized to receive fascia tissue, the recess ending, at a distal end, with a generally proximally facing surface of the shaft configured directly below the narrow portion, the proximally facing surface and the narrow portion shaped and sized to stabilize the trocar in the abdominal wall by the fascia. In some embodiments, a trocar and external cannula assembly are provided. In some embodiments, the trocar and/or trocar and external cannula assembly are configured for deployment of one or more anchors and/or sutures in the tissue.

European patent publication number EP0568098A2 to Greenwald et al. discloses "A trocar incision closure device (10) includes an elongated body (12) having a distal end (20) for insertion through a trocar incised port, a proximal end (14), and a first (70) and second (72) retractable needle holders disposed at the distal end (20) of the body (12). The needle holders (70, 72) are movable between a retracted position and an extended position. An actuator (32) disposed at the proximal end (14) of the body (12) moves the needle holders (70, 72) from the retracted position to the extended position, so that the needle holders (70, 72) can be retracted to allow the device (10) to be inserted through a trocar incision preferably through a cannula inserted into the incised port, and extended to position the needles (56, 58) adjacent the incision, to allow the incision to be sutured."

U.S. Pat. No. 8,109,943 to Boraiah et al. discloses "systems and methods for suture anchor deployment. A system according to the present invention is a trocar system that includes a cannula assembly and an obturator assembly, the cannula assembly providing a needle assembly and the obturator assembly providing a needle actuation mechanism. The obturator assembly may be at least partially inserted into the cannula assembly and arranged to operatively couple the needle actuation mechanism to the needle assembly. The needle assembly includes at least one needle, each needle having disposed near its distal tip a suture anchor. A method according to the present invention includes steps for deploying and/or depositing at least one suture anchor in or through an organ of the human body.

BRIEF SUMMARY

According to a first aspect of the present disclosed subject matter a kit for assembling an incision closing trocar comprising a cannula having a lumen, a proximal side, and a distal side is provided, the kit comprising: an obturator comprising: a shaft having a distal end and a proximal end; at least two anchor recesses are provided near the distal end of the shaft, wherein each anchor recess retains a corresponding anchor; a handle provided at the proximal end of the obturator, is configured to actuate at least two pushers so as to push the corresponding anchors from the anchor recesses; and at least two holders, removably attached to the distal end of the obturator wherein each of the at least two holders holds a coiled or folded suture having a length and one end, wherein the one end of the suture is attached to the corresponding anchor, wherein the length of the suture can be pulled from the holders by removing and pulling away the holder from the obturator, wherein the obturator is sized to be inserted into the lumen of the cannula from the proximal side, together with the at least two holders so that the holders are exposed beyond the distal side when the obturator is fully inserted in the cannula, and then the holders can be removed from the obturator such that the sutures are outside the cannula.

In some exemplary embodiments the at least two corresponding anchors are at least partially within the cannula when the obturator is fully inserted into the cannula.

In some exemplary embodiments the at least two corresponding anchors are fully within the cannula when the obturator is fully inserted into the cannula.

In some exemplary embodiments the at least two holders are joined as a suture cartridge.

In some exemplary embodiments the obturator further comprises an obturator grip having a recess for receiving the suture holders once removed from the distal end.

In some exemplary embodiments the kit further comprises a connecting clip for attaching the suture holders to the cannula, once the holders are removed from the distal end.

In some exemplary embodiments the one end of each of the sutures loops within the anchor forming a closed loop to be secured to the anchor.

According to another aspect of the present disclosed subject matter kit for assembling an incision closing trocar comprising a cannula having a lumen, a proximal side and a distal side is provided, the kit comprising: an obturator comprising: a shaft having a distal end and a proximal end; at least two anchor recesses provided near the distal end, each of the anchor recesses is configured to retain a corresponding anchor; a handle at the proximal end that is configured to actuate at least two pushers for pushing the corresponding anchors from their anchor recesses; an anchor assembly comprises two suture cartridges, each suture cartridge holds a folded or coiled suture having a length and an end, wherein the one end of each suture exits its corresponding suture cartridge and is attached to a corresponding anchor; and an anchor holder holding the anchor such that they can easily be removed from the anchor holder, wherein the obturator is sized to be inserted from the proximal side into the cannula, such that the at least two anchor recesses are within the lumen when the obturator is fully inserted into the cannula, wherein the length of the suture can be pulled out from a corresponding suture cartridge when the anchor holder with the at least two anchors attached to it are pulled away from the anchor assembly, and the anchor holder is sized so that the at least two anchors can be inserted, each to a corresponding anchor recess while the anchors are held by the anchor holder, so that the sutures remain outside the cannula, and wherein the anchor holder can be removed so that each anchor left in its corresponding anchor recess.

In some exemplary embodiments the anchor assembly further comprises connecting member connecting the two suture cartridges, and wherein the connecting member is sized so that the anchor assembly can be attached to an insertion cup of the cannula.

In some exemplary embodiments, the anchor assembly further comprises a sealing set.

In some exemplary embodiments, the anchor assembly is integrated into the obturator.

According to another aspect of the present disclosed subject matter, a method of assembling an incision closing trocar is provided, the method comprising: providing a cannula having a distal side; removing an obturator from a sterile package of a kit; fully inserting the obturator so that at least two holders that removably attached to a distal end of the obturator are exposed beyond the distal side, wherein each holder is provided with a suture; removing the at least two holders from the distal end so that the sutures are pulled out of the holders, and are outside the cannula, while leaving at least two corresponding anchors, each retained within a corresponding recess in the obturator.

In some exemplary embodiments the method further comprising placing the at least two holders on one of: the obturator, the cannula, and the skin of the patient.

In some exemplary embodiments placing the at least two holders on the obturator comprises inserting the at least two holders in a corresponding recess in obturator grip.

In some exemplary embodiments the placing the at least two holders on the cannula comprises attaching the at least two holders to the cannula.

In some exemplary embodiments the placing the at least two holders on the cannula comprises attaching the at least two holders to the cannula.

According to another aspect of the present disclosed subject matter, a kit for assembling an incision closing trocar comprising a cannula having a lumen, a distal side and a proximal side, the kit comprising: an obturator comprising: a shaft having a distal end and a proximal end; at least two anchor recesses provided near the distal end, each recess for retaining a corresponding anchor; a handle at the proximal end is configured to actuate at least two pushers to push the corresponding anchors from their anchor recesses; and at least one coiled or folded suture, removably attached to the distal end, wherein each end of the at least one suture is attached to the corresponding anchor, wherein the at least one suture can be removed from the shaft, and wherein the obturator is sized to be inserted from the proximal side into the cannula, such that the at least one coiled or folded suture is exposed beyond the distal side of the cannula when the obturator is fully inserted into the cannula, and when the at least one suture is pulled from the obturator, the suture remains outside the cannula.

Some exemplary embodiments of the present disclosed subject matter provide a simple to operate kit. Minimal assembly is required, No assembly tools are required. The kit can be used with commercially available cannulas with diameter sufficient to pass the obturator. The length of the shaft of the obturator can be configured to fit the length of the cannula. Standard length and diameter cannulas can be used, but the obturator can be adapted to longer, or lager diameter cannulas. Adaptation of the obturator to thinned cannulas is possible due to the fact that the suture cartridge with integrated releasing mechanism are external to the cannula in some embodiments, or of small size in other embodiments, thus do not interfere with passing the obturator through the cannula. The sutures remain outside the cannula during the surgery, thus not interfering with insertion and operation of the operation tool.

Unless otherwise defined, all technical and scientific terms used herein have the same meaning as commonly understood by one of ordinary skill in the art to which this disclosed subject matter belongs. Although methods and materials similar or equivalent to those described herein can be used in the practice or testing of the present disclosed subject matter, suitable methods and materials are described below. In case of conflict, the specification, including definitions, will control. In addition, the materials, methods, and examples are illustrative only and not intended to be limiting.

The features as indicated above can be combined individually or all together.

BRIEF DESCRIPTION OF THE DRAWINGS

Some embodiments of the disclosed subject matter described, by way of example only, with reference to the accompanying drawings. With specific reference now to the drawings in detail, it is stressed that the particulars shown are by way of example and for purposes of illustrative discussion of the preferred embodiments of the present disclosed subject matter only, and are presented in the cause of providing what is believed to be the most useful and readily understood description of the principles and conceptual aspects of the disclosed subject matter. In this regard, no attempt is made to show structural details of the disclosed subject matter in more detail than is necessary for a fundamental understanding of the disclosed subject matter, the description taken with the drawings making apparent to those skilled in the art how the several forms of the disclosed subject matter may be embodied in practice.

In the drawings:

FIG. 1A(i) schematically illustrates a trocar incision closure kit, in accordance with some exemplary embodiments of the disclosed subject matter;

FIG. 1A(ii) schematically illustrates details of the suture cartridge with integrated releasing mechanism of the trocar incision closure kit, in accordance with some exemplary embodiments of the disclosed subject matter;

FIG. 2A schematically illustrates a trocar incision closure kit having a sealing set, in accordance with some other exemplary embodiments of the disclosed subject matter;

FIGS. 2B(i) to 2B(ii) schematically illustrate steps in assembling the trocar incision closure kit having a sealing set on a cannula, in accordance with some other exemplary embodiments of the disclosed subject matter;

FIGS. 4A(i) to 4A(ii) schematically illustrate the steps of removing a trocar with an incision closure kit from a patient, in accordance with some exemplary embodiments of the disclosed subject matter;

FIG. 4B schematically illustrates incision closure after the operation, in accordance with some exemplary embodiments of the disclosed subject matter;

FIG. 5A schematically illustrates a trocar incision closure kit, in accordance with some exemplary embodiments of the disclosed subject matter;

FIGS. 5B(i) to 5B(iv) schematically illustrate steps in assembling the trocar incision closure kit on a cannula, in accordance with some exemplary embodiments of the disclosed subject matter;

FIGS. 5C(i) to 5C(iv) schematically illustrate illustrates the step of inserting the trocar into the abdominal wall, in accordance with some exemplary embodiments of the disclosed subject matter;

FIGS. 5D(i) to 5D(ii) schematically illustrate the cannula ready for operation, in accordance with some exemplary embodiments of the disclosed subject matter;

FIGS. 6A(i) to 6A(ii) schematically illustrate some details of the obturator handle and pushers mechanism used in an incision closure kit, in accordance with some exemplary embodiments of the disclosed subject matter; and FIGS. 6B(i) to 6B(iii) schematically illustrate some details of a suture cartridge used in an incision closure kit, in accordance with some exemplary embodiments of the disclosed subject matter;

FIG. 7C schematically illustrates the assembled incision closure trocar, in accordance with some other exemplary embodiments of the disclosed subject matter.

DETAILED DESCRIPTION

Figure 1C:
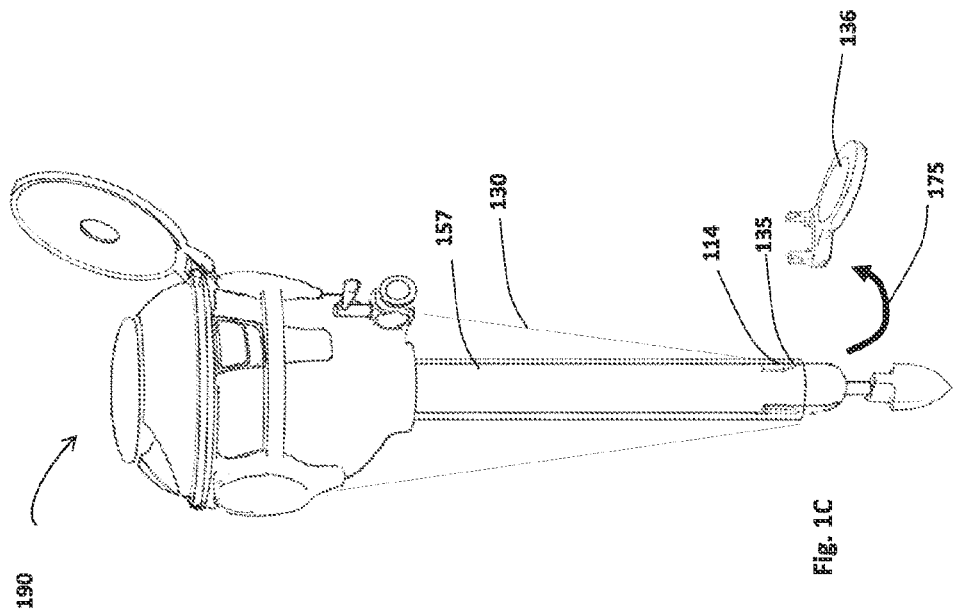
FIG. 1C schematically illustrates the trocar incision closure kit assembled on a cannula having a sealing set, in accordance with some exemplary embodiments of the disclosed subject matter.

Before explaining at least one embodiment of the disclosed subject matter in detail, it is to be understood that the disclosed subject matter is not limited in its application to the details of construction and the arrangement of the components set forth in the following description or illustrated in the drawings. The disclosed subject matter is capable of other embodiments or of being practiced or carried out in various ways. Also, it is to be understood that the phraseology and terminology employed herein is for the purpose of description and should not be regarded as limiting. The drawings are generally not to scale. For clarity, non-essential elements were omitted from some of the drawings.

The terms "comprises", "comprising", "includes", "including", and "having" together with their conjugates mean "including but not limited to". The term "consisting of" has the same meaning as "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this disclosed subject matter may be presented in a range format. It should be understood that the description in range format is merely for convenience and brevity and should not be construed as an inflexible limitation on the scope of the disclosed subject matter. Accordingly, the description of a range should be considered to have specifically disclosed all the possible sub-ranges as well as individual numerical values within that range.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination or as suitable in any other described embodiment of the disclosed subject matter. Certain features described in the context of various embodiments are not to be considered essential features of those embodiments, unless the embodiment is inoperative without those elements.

The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts. A numeral followed by: '; "; ''', or ~ refers to identical or similar element with the same numeral which has been already discussed in a previous figure. These elements may be interchanged.

Definition of terms (for clarity, the suffix ', ", ''', ~ were omitted). In order to remove ambiguity that may be caused by confliction use of terms in the publications of the art, the elements names in the following text and the accompanying figures are as follows: "trocar" is the device (190) ready to be inserted into the patient. The trocar 190 comprises: 1) the "cannula" (150), which can optionally comprise a sealing element, and is the part that stays inserted in the patient during the operation itself, and 2) the obturator (110), which is used during insertion of the trocar into the abdominal wall (310), and then removed. The kits (100, 200, 500) are supplied with the required obturator and other elements (such as suture cartridges (121) or anchor assembly (120, 220) and are used for assembling the trocar using the elements in the kit and an available cannula.

FIG. 1A schematically illustrates a trocar incision closure kit, in accordance with some exemplary embodiments of the disclosed subject matter.

Trocar incision closure kit 100 is generally housed in a sterile package 101 and comprises two main parts: Obturator 110 and anchor assembly 120. Trocar incision closure kit 100 is preferably a disposable kit to be used once during a laparoscopic operation.

Embodiments and functions of obturators, similar to obturator 110 have been disclosed for example in U.S. Pat. No. 10,646,251, which is incorporated herein by reference. The obturator 110 in accordance with some exemplary embodiments of the disclosed subject matter comprises an obturator grip 112 and a handle 111 at the proximal end of a shaft 113. Tip 117, optionally having spikes 116 is connected to the shaft 113 via a neck 115. Two anchor recesses 114 are located at a distal end of shaft 113.

Anchor assembly 120 comprises two suture cartridges with integrated suture pullback/release mechanism 121, each holding folded or coiled suture 130 that is of substantial length, as will be discussed hereinafter. Each suture 130 is attached to an anchor 135. The two anchors 135 are held in an anchor holder 136 such that they can easily be removed from the anchor holder. Pulling the anchor holder 136 away from the anchor assembly 120 releases length of the suture from the suture cartridges. Suture cartridges with integrated suture pullback/release mechanism 121 can have a friction mechanism or a spring-loaded reel to hold the suture prior to pulling anchor holder 136 away from the anchor assembly 120.

A connecting member 122 connects the two suture cartridges with integrated mechanism pullback/release suture thread wire 121. Connecting member 122 can be a ring-like structure or an open "C" shaped structure and may optionally be elastic.

FIG. 1A(ii) schematically illustrates some details of a suture cartridge with integrated suture pullback/release mechanism of the trocar incision closure kit, in accordance with some exemplary embodiments of the disclosed subject matter.

In some embodiments, each suture cartridge comprises a reel 3515 of sutures. In some embodiments, reel 3515 comprises a mechanism for providing automatic pull-back of the sutures, for example during anchor deployment. Optionally, the cartridge further comprises one or more clock springs or torsion spring 3517, operatively coupled to the reel. A potential advantage of storing the sutures on reels 3515 includes reducing the risk of the suture being entangled and/or curled up. In some embodiments, for example at the end of the procedure when the external cannula is removed from the tissue, the suture ends are released from the suture cartridges and can be tied together by a user as seen in FIGS. 4A(ii) and 4B.

Suture pullback/release mechanism 121 can be similar or identical to the mechanism disclosed in U.S. Pat. Nos. 9,636,143, 9,955,997 and 10,646,251, for example, in FIGS. 35C to 35E, which are incorporated herein by reference.

Alternatively, releasing mechanisms 121 may be constructed as seen in FIG. 6B(iii) below.

Figure 1B:
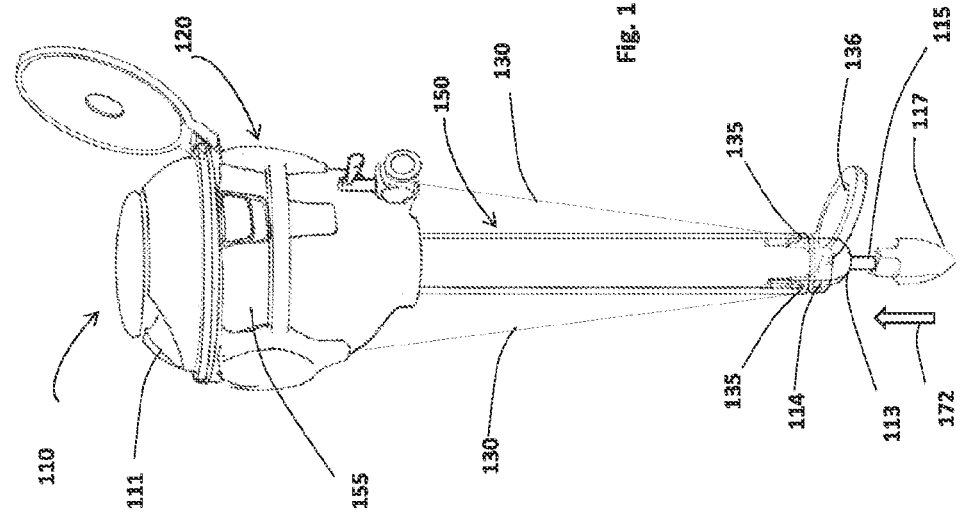
FIGS. 1B(i) to 1B(v) schematically illustrate steps in assembling a trocar incision closure kit on a cannula having a sealing set, in accordance with some exemplary embodiments of the disclosed subject matter.

FIGS. 1B(i) to 1B(v) schematically illustrate steps in assembling the trocar incision closure kit on a cannula having a sealing set, in accordance with some exemplary embodiments of the disclosed subject matter.

The trocar incision closure kit is installed on a cannula 150. The cannula 150 can be a reusable or disposable cannula and can be a standard cannula as known in the art. Cannula 150 comprises an insertion cup 158, optionally having a valve 159, at the proximal end of tube 157.

FIG. 1B(i) schematically illustrates the step 171 (in the figures, the steps are represented by arrows showing the direction of movement of the relevant element/s) of placing anchor assembly 120 in the insertion cup 158.

FIG. 1B(ii) schematically illustrates the anchor assembly 120 placed in the insertion cup 158.

FIG. 1B(iii) schematically illustrates the step 173 of inserting a sealing set 155 into the top opening 156 of the insertion cup 158. Sealing set 155 is preferably the original sealing set that is supplied with cannula 150, and it can optionally include an additional sealing cover 154 for reduced diameter instruments.

FIG. 1B(iv) schematically illustrates the step 174 of inserting the obturator 110 through the sealing set 155 into cannula 150.

FIG. 1B(v) schematically illustrates the obturator 110 inserted into cannula 150 such that its tip 117 and neck 115 protrude beyond the distal end of tube 157.

The user then pulls the anchor holder 136 to release enough length of suture 130 and insert in step 172 the two anchors 135, each in a corresponding anchor recess 114 at the distal end of shaft 113.

FIG. 1C schematically illustrates the trocar incision closure kit assembled on a cannula having a sealing set, in accordance with some exemplary embodiments of the disclosed subject matter.

To complete the assembly, the anchor holder 136 is removed in step 175 leaving the two anchors 135 within the anchor recesses 114. Note that in the assembled trocar 190, the two sutures 130 are outside tube 157.

FIG. 2A schematically illustrates a trocar incision closure kit having a sealing set, in accordance with some other exemplary embodiments of the disclosed subject matter.

According to another aspect of the present disclosed subject matter kit (100,200) for assembling an incision closing trocar (190,190') comprising a cannula (150,150') having a lumen, a proximal side and a distal side is provided, the kit comprising: an obturator (110,110') comprising: a shaft (113,113') having a distal end and a proximal end; at least two anchor recesses (114,114') are provided near the distal end, each of the anchor recesses is configured to retain a corresponding anchor (135,135'); a handle (111,111') at the proximal end that is configured to actuate at least two pushers (321) for pushing the corresponding anchors from their anchor recesses; an anchor assembly (120,220) comprises two suture cartridges (121), each suture cartridge holds a folded or coiled suture (130) having a length and an end, wherein the one end of each suture exits its corresponding suture cartridge and is attached to a corresponding anchor; and an anchor holder (136,136') holding the anchor such that they can easily be removed from the anchor holder, wherein the obturator is sized to be inserted from the proximal side into the cannula, such that the at least two anchor recesses are within the lumen when the obturator is fully inserted into the cannula, wherein the length of the suture can be pulled out from a corresponding suture cartridge when the anchor holder with the at least two anchors attached to it are pulled away from the anchor assembly, and the anchor holder is sized so that the at least two anchors can be inserted, each to a corresponding anchor recess while the anchors are held by the anchor holder, so that the sutures remain outside the cannula, and wherein the anchor holder can be removed so that each anchor is left in its corresponding anchor recess.

In some exemplary embodiments the anchor assembly (120,120') further comprises connecting member (122) connecting the two suture cartridges, and wherein the connecting member is sized so that the anchor assembly can be attached to an insertion cup (158) of the cannula.

In some exemplary embodiments, in the kit (200), the anchor assembly (220) further comprises a sealing set. In some exemplary embodiments, the anchor assembly including holders 121" is integrated into the obturator 110~ as seen in FIG. 7A.

Trocar incision closure kit having a sealing set 200 is generally housed in a sterile package 101' (similar to sterile package 101 seen in FIG. 1A) and comprises two main parts: obturator 110' and anchor assembly with a sealing set 220. Trocar incision closure kit having a sealing set 200 is preferably a disposable kit to be used once during a laparoscopic operation.

Obturator 110' is similar or identical to the obturator 110 seen in the previous figures. The obturator 110' in accordance with some exemplary embodiments of the disclosed subject matter comprises an obturator grip 112' and a handle 111' at the proximal end of a shaft 113'. Tip 117', optionally having spikes 116', is connected to the shaft 113' via a neck 115'. Two anchor recesses 114' are located at a distal end of shaft 113'.

Anchor assembly with sealing set 220 comprises two suture cartridges with integrated suture pullback/release mechanism 121', each holding folded or coiled suture 130 having a significant length. Each suture 130 is attached to an anchor 135. The two anchors 135 are held in an anchor holder 136' such that they can easily be removed from the anchor holder. Pulling the anchor holder 136' away from the anchor assembly with sealing set 220 releases a length of the suture from the suture cartridge using the integrated suture pullback/release mechanism 121'. Suture cartridges with integrated suture pullback/release mechanism 121 can have a friction mechanism or a spring-loaded reel to hold the suture prior to pulling anchor holder 136' away from the anchor assembly with sealing set 220.

Sealing set 155' connects the two suture cartridges.

FIGS. 2B(i) to 2B(ii) schematically illustrate steps in assembling the trocar incision closure kit having a sealing set on a cannula, in accordance with some other exemplary embodiments of the disclosed subject matter.

The cannula 150' can be a reusable or disposable cannula and can be a standard cannula as known in the art. Cannula 150' comprises an insertion cup 158', optionally having a valve 159', at the proximal end of tube 157'. However, cannula 150' need not have a sealing set 155.

FIG. 2B(i) schematically illustrates the step 171' of placing anchor assembly with sealing set 220 in the insertion cup 158'. Additionally, the user pulls the anchor holder 136' to release enough length of suture 130 and inserts in step 172' the two anchors 135' to the distal end of tube 157'.

FIG. 2B(ii) schematically illustrates the step 174' of inserting the obturator 110' through the anchor assembly with sealing set 220 into cannula 150'. When shaft 113' reaches the distal end of tube 157', the two anchors 135' become engaged in the two corresponding anchor recesses 114' that are located at the distal end of shaft 113'.

Figure 2C:
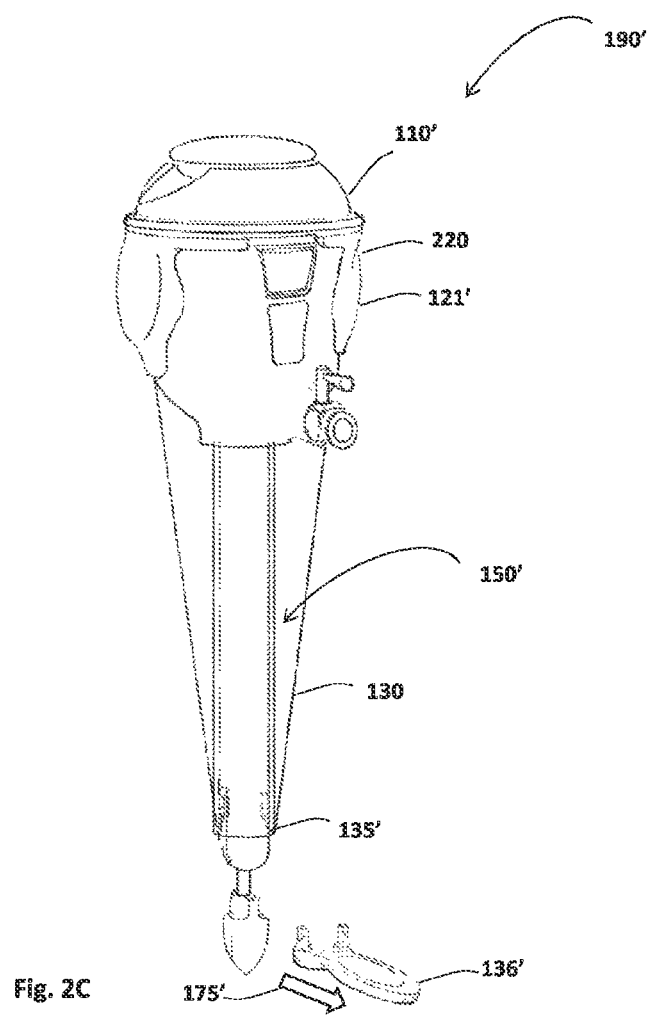
FIG. 2C schematically illustrates the trocar incision closure kit having a sealing set, assembled on a cannula, in accordance with some exemplary embodiments of the disclosed subject matter.

FIG. 2C schematically illustrates the trocar incision closure kit having a sealing set, assembled on a cannula, in accordance with some exemplary embodiments of the disclosed subject matter.

To complete the assembly, the anchor holder 136' is removed in step 175' leaving the two anchors 135' within the anchor recesses 114'. Note that in the assembled trocar 190', the two sutures 130 are outside tube 157'.

Figure 3A:
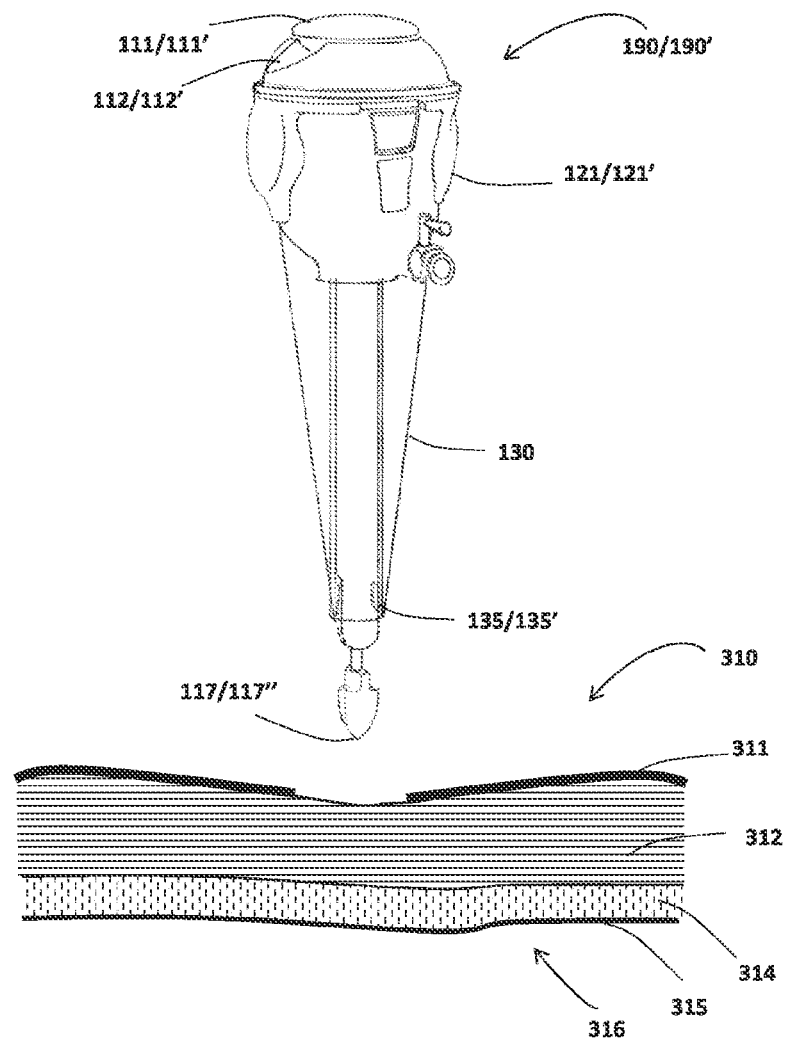
FIGS. 3A(i) to 3A(viii) schematically illustrate the steps of inserting a trocar with an incision closure kit into a patient, in accordance with some exemplary embodiments of the disclosed subject matter.

FIGS. 3A(i) to 3A(viii) schematically illustrate the steps of inserting a trocar with an incision closure kit into a patient, in accordance with some exemplary embodiments of the disclosed subject matter.

FIG. 3A(i) schematically illustrates the placing the assembled trocar 190/190' against the abdominal wall 310 of a patient. Sharp tip 117/117' is optionally capable of penetrating the abdominal wall 310 through the incision.

As known in the art, the abdomen is inflated before inserting a trocar through abdominal wall 130, with gas such as $CO_2$ 316 to separate the abdominal wall 130 from the internal organs (not seen) to be operated on.

Abdominal wall 130 has the following layers: skin 311, a layer of fat 312, fascia (and sometimes muscles) 314, and peritoneum 315. To insert trocar 190/190', an incision is usually made with a scalpel in skin 311 before trocar 190/190' is pushed through the other layers opening its way with the sharp or blunt tip 117/117'. This process is not discussed here in details as it is known from the art.

FIG. 3A(ii) schematically illustrates the assembled trocar 190/190' pushed in the direction represented by arrow 371 to penetrate the abdominal wall 310 of a patient. The distal end shaft 113/113' is within the tissue, while the neck 115/115' has entered the body cavity 313.

FIG. 3A(iii) schematically illustrates the assembled trocar 190/190' pulled back in the direction represented by arrow 372 such that spikes 116/116' are engaged with the inner surface of the abdominal wall tissue.

FIG. 3A(iv) schematically illustrates cocking the assembled trocar 190/190' by pulling the handle 111/111' in the direction represented by arrow 373 upwardly while leaving obturator grip 112/112' in the same position, leaving trocar 190/190' engaged with the abdominal wall 310.

FIG. 3A(v) schematically illustrates deploying anchors 135/135' by pressing in the direction represented by arrow 374 the handle 111/111' downwardly towards obturator grip 112/112'. This action moves the two pushers 321 that deploy anchors 135/135' in the direction represented by arrow 375 from the anchor reassess 114/114'. Optionally, a short length of suture 130 is released from the suture cartridges with integrated suture pullback/release mechanism 121/121'.

FIG. 3A(vi) schematically illustrates engaging anchors 135/135' in the direction represented by arrow 377 with the abdominal wall tissue 310 by pulling in the direction represented by arrow 376 the two sutures 130 after the pushers had retracted back into the shaft 113/113' of the assembled trocar 190/190'.

FIG. 3A(vii) schematically illustrates insertion of the tube 157/157' into the abdominal wall 310 by pushing the assembled trocar 190/190' in the direction represented by arrow 378.

Finally, FIG. 3A(viii) schematically illustrates the cannula 150/150' ready for operation when obturator 110/110' is removed as shown by arrow 379 from the cannula 150/150'.

Figure 3B:
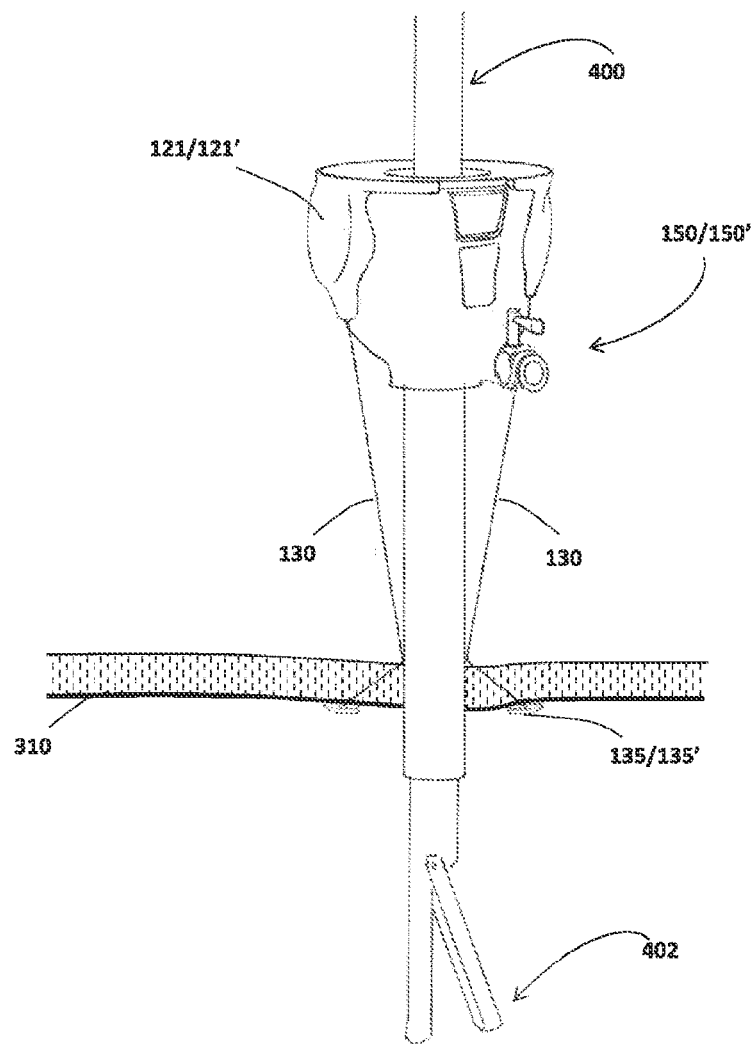
FIG. 3B schematically illustrates using the trocar incision closure kit during operation, in accordance with some exemplary embodiments of the disclosed subject matter.

FIG. 3B schematically illustrates using the cannula 150/150' with incision closure kit during operation, in accordance with some exemplary embodiments of the disclosed subject matter.

Operation instrument 400 is inserted into the cannula 150/150' through the sealing set 155/155' and the user can perform laparoscopic procedure by operating a tool 402 at the distal end of instrument 400.

Optionally, sutures 130 that are anchored to the abdominal wall 310 by anchors 135/155' are kept tight by locking the suture releasing mechanism within the suture cartridges with integrated suture pullback/release mechanism 121/121', thus helping to secure cannula 150/150' in place.

FIGS. 4A(i) to 4A(ii) schematically illustrate the steps of removing a trocar with an incision closure kit from a patient, in accordance with some exemplary embodiments of the disclosed subject matter.

FIG. 4A(i) schematically illustrates removing cannula 150/151' in the direction represented by arrow 571. Preferably, sutures 130 are released from the suture cartridges using the integrated suture pullback/release mechanism 121/121' or are cut.

FIG. 4A(ii) schematically illustrates the open incision port 319 left in abdominal wall 310 after removal of the cannula, while sutures 130 are anchored to the sides of the incision by anchors 135/135'.

Finally, FIG. 4B schematically illustrates incision closure after the operation, in accordance with some exemplary embodiments of the disclosed subject matter. Sutures 130 are connected with a knot 410 such that anchors 135/153' pulls the incision port 319 so as to be tight closed.

FIG. 5A schematically illustrates a trocar incision closure kit 500, in accordance with some exemplary embodiments of the disclosed subject matter.

According to a first aspect of the present disclosed subject matter a kit (500) for assembling an incision closing trocar (190",190''') comprising a cannula (150") having a lumen, a proximal side, and a distal side is provided, the kit comprising: an obturator comprising: a shaft (113') having a distal end and a proximal end; at least two anchor recesses (114") are provided near the distal end of the shaft, wherein each anchor recess retains a corresponding anchor (135"); a handle (111") provided at the proximal end of the obturator, is configured to actuate at least two pushers (321,321") so as to push the corresponding anchors from the anchor recesses; and at least two holders (610), removably attached to the distal end of the obturator wherein each of the at least two holders holds a coiled or folded suture (630) having a length and one end, wherein the one end of the suture (130) is attached to the corresponding anchor, wherein the length of the suture can be pulled from the holders by removing and pulling away the holder from the obturator, wherein the obturator is sized to be inserted into the lumen of the cannula from the proximal side, together with the at least two holders so that the holders are exposed beyond the distal side when the obturator is fully inserted in the cannula, and then the holders can be removed from the obturator such that the sutures are outside the cannula.

In some exemplary embodiments the at least two corresponding anchors are at least partially within the cannula when the obturator is fully inserted into the cannula.

In some exemplary embodiments the at least two corresponding anchors are fully within the cannula when the obturator is fully inserted into the cannula.

In some exemplary embodiments the at least two holders (610) are joined as a suture unit (121").

In some exemplary embodiments the obturator (110") further comprises an obturator grip (112") having a recess (521) for receiving the suture unit (121") once removed from the distal end.

In some exemplary embodiments the kit further comprises a connecting clip for attaching the suture unit (121") to the cannula or obturator, once the holders are removed from the distal end.

In some exemplary embodiments the one end of each of the sutures (130) loops within the anchor forming a closed loop to be secured to the anchor.

Trocar incision closure kit 500 is generally housed in a sterile package 101" and comprises obturator 110"/110'''. In contrast to the embodiments in which the suture cartridges with the integrated suture pullback/release mechanism 121/121' were separated and part of an anchor assembly 120, obturator 110"/110''' is already fitted with anchors 135" and suture unit 121". Trocar incision closure kit 500 is preferably a disposable kit to be used once during a laparoscopic operation.

Obturator 110"/110''' together with anchors 135", which are connected by sutures 130 to the suture cartridges, is narrow enough to be inserted into a standard cannula.

The obturator 110"/110''' in accordance with some exemplary embodiments of the disclosed subject matter comprises an obturator grip 112" and a handle 111" at the proximal end of a shaft 113", and tip 117" located at the distal end of shaft 113".

Construction and operation of obturator 110" is similar or identical to that of obturator 110 and 110' and will be disclosed in more details in FIGS. 6A(i) to 6A(ii).

Construction and operation of the suture unit 121" will be disclosed in more details in FIGS. 6B(i) to 6B(iii).

FIGS. 5B(i) to 5B(iv) schematically illustrate steps in assembling the trocar incision closure kit 500 on a cannula, in accordance with some exemplary embodiments of the disclosed subject matter.

According to another aspect of the present disclosed subject matter, a method of assembling an incision closing trocar (190",190''') is provided, the method comprising: providing a cannula (150") having a distal side; removing an obturator (110",110''') from a sterile package (101") of a kit (500); fully inserting (174) the obturator so that at least two holders (610) that removably attached to a distal end of the obturator are exposed beyond the distal side, wherein each holder is provided with a suture (130); removing the at least two holders from the distal end so that the sutures are pulled out of the holders, and are outside the cannula, while leaving at least two corresponding anchors (135"), each retained within a corresponding recess (114") in the obturator.

In some exemplary embodiments the method further comprising placing (570,570') the at least two holders on one of: the obturator, the cannula, and the skin (310) of the patient.

In some exemplary embodiments placing (570) the at least two holders on the obturator comprises inserting the at least two holders in a corresponding recess (521) in obturator grip (112").

In some exemplary embodiments the placing (570') the at least two holders on the cannula comprises attaching (570') the at least two holders to the cannula (150").

In some exemplary embodiments the placing (570') the at least two holders on the cannula comprises attaching (570') the at least two holders to the cannula (150").

FIG. 5B(i) schematically illustrates the step represented by an arrow 174" of inserting the obturator 110" into cannula 150".

The obturator 110" in trocar incision closure kit 500 is installed on a cannula 150". The cannula 150" can be a reusable or disposable cannula and can be a standard cannula as known in the art. Cannula 150" comprises an insertion cup 158" at the proximal end of tube 157".

The obturator 110", together with anchors 135", sutures 130 and the suture unit 121" is inserted into the lumen of cannula 150".

FIG. 5B(ii) schematically illustrates the obturator 110" inserted into cannula 150" such that its tip 117", and the suture unit 121" protrude beyond the distal end of tube 157".

A length of suture 130 is pulled out of the suture cartridges with suture integrated folding mechanism 121". The suture cartridges with suture integrated folding mechanism 121" are attached by the user to obturator 110" or cannula 150", while two optional and preferable locations for the attachments are shown herein below.

FIG. 5B(iii) schematically illustrates the suture unit 121" that are being transferred as indicated by arrow 570 from the lower portion of the obturator and into a corresponding recess 521 in obturator grip 112" of the obturator 110". Note that sutures 130 remain outside cannula 150", and anchors 135" remain in their corresponding recesses in the lower portion of obturator 110" as was the case in the previously disclosed embodiments.

The assembled trocar 190" is now ready to be inserted into the abdomen of the patient.

FIG. 5B(iv) schematically illustrates the suture unit 121" is transferred as indicated by arrow 570' and attached to the tube 157" of cannula 150". An elastic band or adhesive tape can be used for attaching the suture cartridges to the tube 157" of cannula 150". Optionally, a connecting clip (not seen here) can be provided with the kit 500 and used for attaching the suture unit 121" to cannula 150". Note that sutures 130 remain outside cannula 150", and anchors 135" remain in their corresponding recesses in the lower portion of obturator 110''' as was the case in the previously disclosed embodiments.

Other locations are possible to place the cartridges with the sutures without limiting the scope of the present disclosure. Alternatively, the suture unit 121" can be simply placed to rest on the skin 311 of the patient near trocar 190"/190''' as will be shown hereinafter.

Alternatively, sutures 130 are completely pulled out of the suture cartridges which is then discarded.

Yet alternatively, sutures 130 are cut and the suture cartridges is then discarded.

Then, the assembled trocar 190''' is ready to be inserted into the incision in the patient's abdomen.

FIGS. 5C(i) to 5C(iv) schematically illustrate the steps of inserting the trocar into the abdominal wall, in accordance with some exemplary embodiments of the disclosed subject matter.

These steps generally follow the steps disclosed in FIGS. 3A(i) to 3A(viii).

FIG. 5C(i) schematically illustrates the assembled trocar 190"/190''' penetrating the abdominal wall 310 of a patient, similarly to as seen in FIG. 3A(iii).

FIG. 5C(ii) schematically illustrates cocking the assembled trocar 190"/190''' by pulling as indicated by arrow 373' the handle 111" upwardly to engage the slider at the end of stroke that than can deploy the pushers while leaving obturator grip 112" in the same position, leaving trocar 190"/190''' engaged with the abdominal wall 310, similarly to as seen in FIG. 3A(iv).

FIG. 5C(iii) schematically illustrates deploying anchors 135" by pressing as indicated by arrow 134' the handle 111" downwardly towards obturator grip 112". This action moves two pushers 321" in a direction as indicated by arrow 375" that deploy anchors 135" from the anchor recess 114", similarly to as seen in FIG. 3A(v)

FIG. 5C(iv) schematically illustrates retracting as indicated by arrow 570 the two pushers 321" by pressing handle 111" all the way downwardly as indicated by arrow 571 towards obturator grip 112", similarly to as seen in FIG. 3A(vi).

Some details of the actions seen in FIGS. 5C(iii) and 5C(iv) are further explained in the explanation to FIGS. 6A(i) to 6A(ii).

FIG. 5C(v) schematically illustrates insertion of the tube 157" into the abdominal wall 310 by pushing as indicated by arrow 378" the assembled trocar 190"/190''', similarly to as seen in FIG. 3A(vii)

Finally, FIG. 5C(vi) schematically illustrates the cannula 150" that is ready for operation when obturator 110"/110''' is removed as indicated by arrow 379" from the cannula 150", similarly to as seen in FIG. 3A(viii).

In the case where the unit 121" is attached to obturator 110" as seen in FIG. 5C(i), it may be removed and simply placed to rest on the skin 311. Alternatively, sutures 130 are completely pulled out of the suture unit 121" that is then discarded. Alternatively, sutures 130 are cut and suture unit 121" is then discarded.

FIGS. 5D(i) to 5D(ii) schematically illustrate the cannula 150" ready for operation, in accordance with some exemplary embodiments of the disclosed subject matter.

FIG. 5D(i) schematically illustrates the sutures 130 with free ends 519.

FIG. 5D(ii) schematically illustrates the sutures 130 connected to the suture unit 121" that is attached to cannula 150".

FIG. 5D(iii) schematically illustrates the sutures 130 connected to the suture unit 121" that is resting on the skin 311.

Using the cannula for operation and incision closure after the operation follows the same process illustrated in FIGS. 3B to 4B.

FIGS. 6A(i) to 6A(ii) schematically illustrate some details of the obturator handle and pushers mechanisms used in an incision closure kit, in accordance with some exemplary embodiments of the disclosed subject matter.

Obturator handle and pushers mechanisms can be similar or identical to mechanisms disclosed in U.S. Pat. Nos. 9,636,143, 9,955,997 and 10,646,251, for example in some of FIGS. 10, 11A to 11B, 16A to 18, and 26A to 28E, which are incorporated herein by reference.

In the following figures, the tubular body of obturator 110/110'/110"/110''' was removed so as not to clatter the figure and to reveal the inner mechanism of obturator 110/110'/110"/110'''.

FIG. 6A(i) schematically illustrates a cross section of the obturator 110/110'/110"/110''' being cocked 379/379", in accordance with some exemplary embodiments of the disclosed subject matter.

Enlargement of the central section 691 of the obturator is seen in more details in FIG. 6A(ii).

FIG. 6A(ii) schematically illustrates a cross section of the enlarged central section 691 during the cocking stage.

As the handle 111 is pulled upwardly as indicated by arrow 379/379", spring 692 located around the first shaft 611 is stretched. Handle 111 can be pulled until its lower end 612 is engaged with the upper end 614 of the pusher structure 613 that terminates in two pushers 321. Each pusher 321 is engaged with a corresponding anchor 135.

Spacer 660 is used as fixture to allow the handle 111 to be pulled while extending the spring 692.

The obturator 110/110'/110"/110''' as handle 111 can be pushed to extend the pushers 321, in accordance with some exemplary embodiments of the disclosed subject matter.

When the handle 111 is pushed down, initially the end 612 of first shaft 611 pushes the pusher structure 613 and the two pushers 321 downwardly to deploy the two anchors 135.

Spacer 660 can slide downwardly until the handle 111 is slightly 674 above the top of the obturator grip 112. When handle 111 is pushed all the way down, the notches 671 on first shaft 611 meet the notch 672 in the central shaft 673 of obturator 110/110'/110"/110'''. This allows the wings 675 to move inwardly, releasing the pusher structure 613, and thus the pusher structure 613 and the two pushers 321 are puled upwards by spring 692 into the body of obturator 110/110'/ 110"/110'''.

FIGS. 6B(i) to 6B(iii) schematically illustrate some details of a suture unit 121" used in an incision closure kit 500, in accordance with some exemplary embodiments of the disclosed subject matter.

According to another aspect of the present disclosed subject matter, a kit (500) for assembling an incision closing trocar (190", 190''') comprising a cannula (150") having a lumen, a distal side and a proximal side, the kit comprising: an obturator comprising: a shaft (113') having a distal end and a proximal end; at least two anchor recesses (114") provided near the distal end, each recess for retaining a corresponding anchor (135"); a handle (111") at the proximal end is configured to actuate at least two pushers (321, 321") to push the corresponding anchors from their anchor recesses; and at least one coiled or folded suture (130), removably attached to the distal end, wherein each end of the at least one suture (130) is attached to the corresponding anchor, wherein the at least one suture can be removed from the shaft, and wherein the obturator is sized to be inserted from the proximal side into the cannula, such that the at least one coiled or folded suture is exposed beyond the distal side of the cannula when the obturator is fully inserted into the cannula, and when the at least one suture is pulled from the obturator, the suture remains outside the cannula.

FIG. 6B(i) schematically illustrates the obturator 110"/ 110''' used in kit 500, in accordance with some exemplary embodiments of the disclosed subject matter.

Enlargement of the distal section 601 of obturator 110"/ 110''' is seen in more details in FIG. 6B(ii).

FIG. 6B(ii) schematically illustrates enlargement of the distal section 601 of obturator 110"/110''', in accordance with some exemplary embodiments of the disclosed subject matter.

Distal end of shaft 113" has two anchor recesses 114" (only one is seen herein), to fit the two anchors 135" (only one is seen herein). Each anchor 135" is connected to a corresponding suture 130 which is coiled or folded within a corresponding holder 610 of the suture unit 121".

Anchors 135" can be released from anchor recesses 114" when the pushers (not seen herein) push them out.

Cartridges with the suture unit 121" can be manually removed from shaft 113" as seen in FIGS. 5B(iii) and 5B(iv).

Optionally, the end of suture 130 may be looped through a hole or holes in the anchor 136 and tide to remaining of suture 130 thus being secured to the anchor 136. Other methods of securing suture 130 to the anchor 136 may be used.

FIG. 6B(iii) schematically illustrates enlargement of a cross section of the suture unit 121", in accordance with some exemplary embodiments of the disclosed subject matter.

Within each holder 610 of the suture unit 121", a coiled or folded 630 suture 130 having a length is provided. Suture 130 exits holder 610 via a small opening 620.

Optionally, an elastomer element 640 is connected to the end of the suture that is coiled or folded 630 to its respective holder 610 to keep the suture under slight tension when fully extended. Alternatively, the end of the coiled or folded suture is not connected to the respective holder 610 and is free to be pulled away from the suture unit 121".

Optionally, connecting member 650 connects the two compartments 610 of the suture unit 121" together. Optionally, connecting member 650 is flexible and allows attaching and detaching of the suture unit 121" to and from shaft 113". Optionally, the two compartments 610 of the suture unit 121" can be manually separated. Optionally, the two compartments 610 are separated.

Optionally, suture unit 121" are used with the embodiments detailed in FIGS. 1 and 2 instead of using reels and clock springs. It should be mentioned that other folding or coiling mechanisms can be used in a compartment or without a compartment without limiting the scope of the present disclosure.

Optionally, suture unit 121" may be missing and the length of suture may be simply folded and held to shaft 113", for example with adhesive tape.

Optionally, suture 130 may be a single length of suture, connected in each end to a corresponding anchor 135.

FIG. 7A schematically illustrates a trocar incision closure kit 700, in accordance with some other exemplary embodiments of the disclosed subject matter.

Trocar incision closure kit 700 is generally housed in a sterile package 101~ (similar to sterile packages 101 seen in previous figures).

However, obturator 110~ is already in assembled state with suture holders 121~ already attached to obturator grip 112~.

Suture unit 121~, can comprise any one of the other elements 121, 121', 121". Alternatively, suture unit 121~, can be in the form of a simple, not enclosed holder for a coiled or folded length of suture 130.

Each suture 130 is attached to an anchor 135~. The two anchors 135~ are held in an anchor holder 136~ such that they can easily be removed from the anchor holder. Pulling the anchor holder 136~ away from suture holders 121~ so as to release a length of suture 130.

Figure 7B:
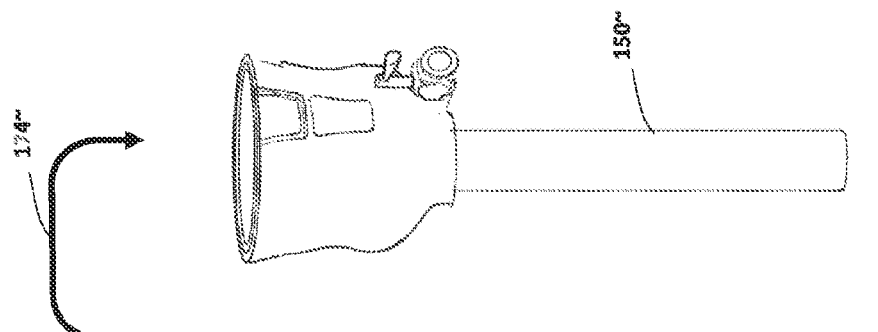
FIGS. 7B(i) to 7B(iii) schematically illustrate steps in assembling the trocar incision closure kit on a cannula, in accordance with some exemplary embodiments of the disclosed subject matter.
Figure 7A:
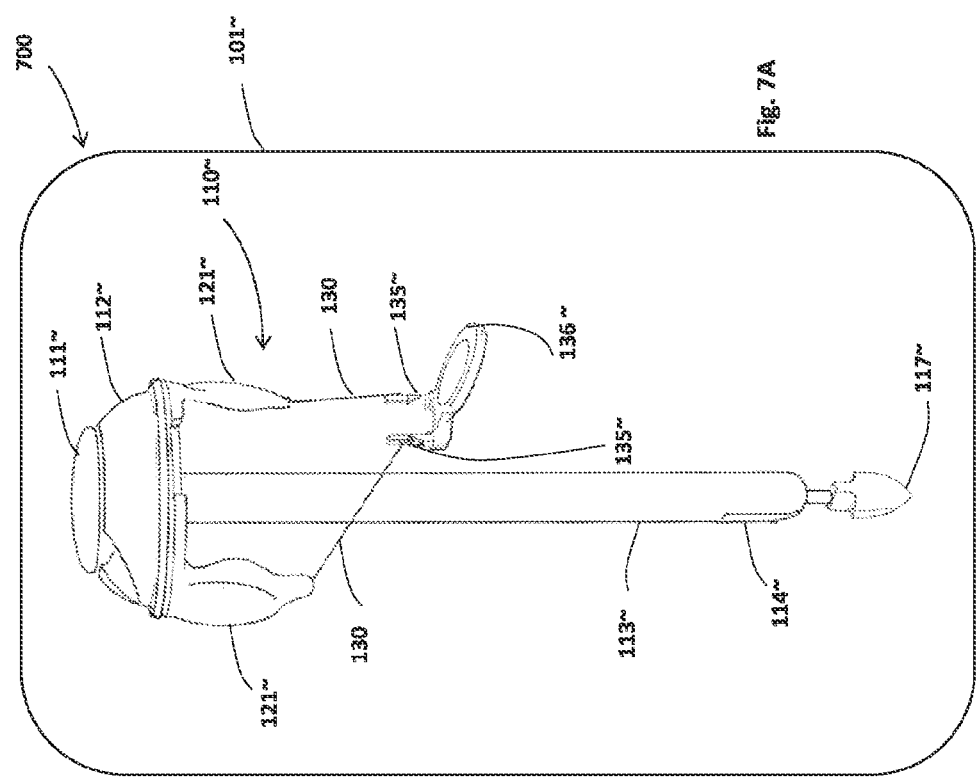
FIG. 7A schematically illustrates a trocar incision closure kit, in accordance with some other exemplary embodiments of the disclosed subject matter.

FIGS. 7B(i) to 7B(iii) schematically illustrate steps in assembling the trocar incision closure kit on a cannula, in accordance with some exemplary embodiments of the disclosed subject matter.

FIG. 7B(i) schematically illustrates a step in assembling the trocar incision closure kit on a cannula, in accordance with some exemplary embodiments of the disclosed subject matter.

To assemble the incision closure trocar, the user first inserts as indicated by arrow 174~ the obturator 110~ into cannula 150~.

FIG. 7B(ii) schematically illustrates another step in assembling the trocar incision closure kit on a cannula, in accordance with some exemplary embodiments of the disclosed subject matter.

The user pulls the anchor holder 136~ as indicated by arrow 774 such that anchor holder 136~ is below the distal end of the shaft 113~ of obturator 110~.

FIG. 7B(iii) schematically illustrates another step in assembling the trocar incision closure kit on a cannula, in accordance with some exemplary embodiments of the disclosed subject matter.

The user inserts the anchors 135~ into the anchor recesses 114~ in shaft 113~ of obturator 110~, such that sutures 130 remain outside cannula 150~.

FIG. 7C schematically illustrates the assembled incision closure trocar 190~, in accordance with some exemplary embodiments of the disclosed subject matter.

Finally, the user removes the anchor holder 136~ as indicated in arrow 175~, leaving the anchors 135~ in the anchor recesses 114~ such that the assembled incision closure trocar 190~ is ready to be used as seen in FIGS. 3A(i) to 3A(viii).

Optionally, the kits seen in each of FIGS. 1A, 2A, 5A, 7A, may include a disposable cannula, supplied as part of the kit, inside the sterile same sterile package 101, or in another sterile package.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A kit for assembling an incision closing trocar comprising a cannula having a lumen, a cannula proximal side, and a cannula distal side, the kit comprising:
    an obturator comprising:
        a shaft having a distal end and a proximal end;
        at least two anchor recesses provided near the distal end of said shaft, wherein each anchor recess retains a corresponding anchor;
        a handle provided at the proximal end configured to actuate at least two pushers to push the corresponding anchors from the anchor recesses; and
        at least two holders removably attached to the distal end wherein each of the at least two holders holds a coiled or folded suture having a length and one end, wherein the one end is attached to the corresponding anchor, and wherein the length can be pulled from the holders by removing and pulling away each holder from the obturator,
    wherein said obturator is sized to be inserted into the lumen of the cannula from the proximal side, together with said at least two holders so that the holders are exposed on the exterior of the distal end of the obturator, beyond the distal side when the obturator is fully inserted in the cannula, and wherein the holders can be removed from the obturator such that the sutures are outside the cannula.

2. The kit of claim 1, wherein said at least two corresponding anchors are at least partially within the cannula when said obturator is fully inserted into the cannula.

3. The kit of claim 1, wherein said at least two corresponding anchors are fully within the cannula when said obturator is fully inserted into the cannula.

4. The kit of claim 1, wherein said at least two holders are joined as a suture unit.

5. The kit of claim 4, wherein said obturator further comprises an obturator grip having a recess for receiving said suture unit once removed from said distal end.

6. The kit of claim 4, wherein the kit further comprises a connecting clip for attaching the suture unit to the cannula, once the holders are removed from said distal end.

7. The kit of claim 1, wherein said one end loops within the anchor while forming a closed loop to be secured to said corresponding anchor.

* * * * *